(12) United States Patent
Sultanov et al.

(10) Patent No.: US 12,116,395 B2
(45) Date of Patent: Oct. 15, 2024

(54) KCNV2 VARIANTS AND THEIR USE

(71) Applicant: Artema Therapeutics, Inc., Brooklyn, NY (US)

(72) Inventors: Shamil Sultanov, Paphos (CY); Maria Sultanova, Paphos (CY); Livia Carvalho, Nedlands (AU); David Hunt, Nedlands (AU); Rabab Rashwan, Nedlands (AU); Pavel Y. Volchkov, Moscow (RU)

(73) Assignee: Artema Therapeutics, Inc., Brooklyn, NY (US)

( * ) Notice: Subject to any disclaimer, the term of this patent is extended or adjusted under 35 U.S.C. 154(b) by 0 days.

(21) Appl. No.: 17/748,611

(22) Filed: May 19, 2022

(65) Prior Publication Data

US 2022/0372100 A1 Nov. 24, 2022

Related U.S. Application Data

(60) Provisional application No. 63/191,106, filed on May 20, 2021.

(51) Int. Cl.
| | | |
|---|---|---|
| *C07K 14/705* | (2006.01) | |
| *A61K 38/00* | (2006.01) | |
| *C12N 15/86* | (2006.01) | |

(52) U.S. Cl.
CPC ............ *C07K 14/705* (2013.01); *C12N 15/86* (2013.01); *A61K 38/00* (2013.01); *C12N 2750/14122* (2013.01); *C12N 2750/14142* (2013.01); *C12N 2750/14145* (2013.01)

(58) Field of Classification Search
CPC .................. C07K 14/705; C12N 15/86; C12N 2750/14122; C12N 2750/14142; C12N 2750/14145; A61K 38/00
See application file for complete search history.

*Primary Examiner* — Titilayo Moloye
*Assistant Examiner* — Gillian C. Reglas
(74) *Attorney, Agent, or Firm* — Schafer IP Law PLLC

(57) ABSTRACT

Disclosed herein are novel variants of KCVN2 and their use, for example, in methods of treating a subject with a retinal disorder, such as CDSRR.

13 Claims, 21 Drawing Sheets
Specification includes a Sequence Listing.

FIG. 7

| Group | N eyes | Treatment | Animal strain | Age | Dose, Volume | OCT follow-up | Scotopic ERG follow up weeks | Photopic ERG follow up weeks | Histology (n=5) | qRT-PCR (n=5) |
|---|---|---|---|---|---|---|---|---|---|---|
| A | 15 | AAV2/8-RK-KCNV2 | KCNV2 KO | 28-35 days | 1 µl (1x10$^{12}$ GC/mL) | • 0-3 days post injection • 2 weeks • 12 weeks | • 3-4 weeks • 7-8 weeks • 11-12 weeks | • 3-4 week • 11-12 weeks | 12 weeks | 12 weeks |
| B | 15 | PBS | As above | As above | 1 µl | As above | As above | As above | As above | As above |
| C | 15 | None | As above | As above | None | As above | As above | As above | As above | As above |

FIG. 11

```
▓▓▓CTCAAACAGAGTGAGAGGAGAGACGGTCCTGGAGCTACAGGCCCTGGAACACGACGGAGAA
▓▓▓CTGAAGCAGAGTGAGAGGAGGAGGTCATGGAGTTATCGACCTTGGAACACGACTGAAAA

TGAGGGCAGCCAACACCGCAGGAGCATTTGCTCCCTGGGTGCCCGTTCCGGCTCCCAGGCCA
CGAAGGCAGCCAGCATCGCAGATCCATTTGCTCCCTGGGGCCGCAGTGGCTCACAAGCGT

GCATCCACGGCTGGACAGAGGCAACTATAACTACTACATCGAGGAAGACGAAGACGGCGAG
CCATCCACGGCTGGACTGAAGGAAATTATAACTACTATATAGAGGACGACGAAGACGGAGAG

GAGGAGGACCAGTGGAAGGACGACCTGGCAGAAGAGGACCAGCAGGCAGGGAGGTCACCAC
GAGGAAGACCAATGGAAGATGATCTGGCGGAGGAAGATCAGCAAGCGGTGAAGTGACCAC

CGCCAAGCCCGAGGGCCCCAGCGACCCTCCGGCCCTGCTGTCCACGCTGAATGTGAACGTGG
TGCTAAACCCGAAGGACCATCTGACCCACCTGCACTCTTGAGCACATTGAATGTAAATGTTG

GTGGCCACAGCTACCAGCTGGACTACTGCGAGCTGGCCGGCTTCCCAAGACGCGCCTAGGT
GGGGTCACAGCTACCAATTGGATTACTGCGAGCTTGCCGGGTTTCCCAAGACTCGGCTCGGA

CGCCTGGCCACCTCCACCAGCCGCAGCCGCCAGCTAAGCCTGTGCGACGACTACGAGGAGCA
AGCTCGCAACATCCACAAGCAGGTCCGGCAATTGTCACTGTGCGATGACTATGAAGAACA

GACAGACGAATACTTCTTCGACCGCGACCCGGCCGTCTTCCAGCTGGTCTACAATTTCTACC
AACAGACGAGTATTTCTTTGACAGGGACCCGGCTGTCTTCCAGTTGGTCTATAACTTCTATC

TGTCCGGGGTGCTGCTGGTGCTCGACGGGCTGTGTCCGGCCGCTTCCTGGAGGAGCTGGGC
TGTCAGGTGTTCTCCTCGTTCTCGATGGCCTGTGTCCTCGGCGATTCTTGGAAGAACTCGGG

TACTGGGGCGTGCGGCTCAAGTACACGCCACGCTGCTGCCGCATCTGCTTCGAGGAGCGGCG
TACTGGGGGGTGAGGTTGAAATATACCCCTCGGTGCTGCCGCATTTGTTTGAGGAAAGGCG

CGACGAGCTGAGCGAACGGCTCAAGATCCAGCACGAGCTGCGCGCGCAGGCGCAGGTCGACG
AGATGAGCTTTCAGAGCGGTTGAAGATACAACACGAACTTAGAGCGCAGGCTCAGGTAGAAG

AGGCGGAGGAACTCTTCCGCGACATGCGCTTCTACGGCCCGCAGCGGCGCCGCCTCTGGAAC
AAGCTGAAGAATTGTTTCGAGACATGAGATTTTATGGCCCACAGCGCCGCCGGCTGTGGAAC

CTCATGGAGAAGCCATTCTCCTCGGTGGCCGCCAAGGCCATCGGGGTGGCCTCCAGCACCTT
CTCATGGAAAAGCCTTTCTCAAGTGTGGCCGCCAAGGCTATTGGCGTTGCCAGCAGCACTTT

CGTGCTCCGTCTCCGTGGTGGCGCTGGCGCTCAACACCGTGGAGGAGATGCAGCAGCACTCGG
CGTACTTGTGAGCGTAGTGGCACTGGCATTGAATACTGTAGAGGAGATGCAGCAGCACAGCG
```

FIG. 20

```
GGCAGGCGAGGCGGCCAGACCTGCGGCCATCCTGGAGCACGTGGAGATGCTCTGCATG
GACAGGGTGAAGGCGGCCCTGACCTTCGGCCTATCCTCGAACATGTCGAAATGCTCTGCATG

GGCTTCTTCACGCTCGAGTACCTGCTGCGCCTAGCCTCCACGCCCGACCTGAGGCGCTTCGC
GGCTTTTTCACCTTCGAGTACCTTCTTCGACTTGCATCTACGCCAGACTTGCGGAGATTTGC

GCGCAGCGCCCTCAACCTGGTGGACCTGGTGGCCATCCTGCCGCTCTACCTTCAGCTGCTGC
TAGGAGCGCTCTTAACCTGGTTGACCTCGTCGCGATCCTGCCGTTGTACCTCCAGCTGCTTC

TCGAGTGCTTCACGGCGAGGCCACCAACGCGGCCAGACGGTGGGCAGCGTGGGTAAGGTG
TCGAGTGTTTACAGGTGAGGGTCACCAACGCGGCCAGACTGTCGGGAGCGTCGGAAAGGTT

GGTCAGGTGTTGCGCGTCATGCGCCTCATGCGCATCTTCCGCATCCTCAAGCTGGCGCGCCA
GGTCAGGTTCTGCGCGTCATGAGATTGATGAGGATATTTAGAATCCTCAAATTGGCTAGACA

CTCCACCGGACTGCGTGCCTTGGGCTTCACGCTGCGCCAGTGCTACCAGCAGGTGGGCTGCC
TAGTACTGGGTTGCGCGCATTCGGTTTCACCCTTCGACAGTGCTATCAGCAAGTTGGGTGCT

TGCTGCTCTTCATCGCCATGGGCATCTTCACTTTCTCTGCGGCTGTCTACTCTGTGGAGCAC
TGCTCTTGTTCATCGCTATGGGAATCTTCACTTTTTCCGCCGCCGTATATTCCGTAGAACAT

GATGTGCCCAGCACCAACTTCACTACCATCCCCCACTCCTGGTGGTGGGCCGCGGTGAGCAT
GACGTTCCCTCCACCAATTTTACAACAATCCCGCATAGCTGGTGGTGGGCTGCTGTCTCCAT

CTCCACCGTGGGCTACGGAGACATGTACCCAGAGACCCACCTGGGCAGGTTTTTTGCCTTCC
CTCTACGGTCGGCTACGGCGACATGTACCCCGAAACGCACCTCGGTAGGTTCTTCGCATTTC

TCTGCATTGCTTTTGGGATCATTCTCAACGGGATGCCCATTTCCATCCTCTACAACAAGTTT
TGTGCATCGCCTTTGGAATCATTCTTAATGGTATGCCTATTTCAATACTTTACAATAAATTC

TCTGATTACTACAGCAAGCTGAAGGCTTATGAGTATACCACCATACGCAGGGAGAGGGGAGA
TCCGATTACTACAGTAAATTGAAAGCATACGAGTATACTACCATTCGGCGCGAGAGGGGCGA

GGTGAACTTCATGCAGAGAGCCAGAAAGAAGATAGCTGAGTGTTTGCTTGGAAGCAACCCAC
AGTAAATTTCATGCAGCGAGCAAGAAAAAAATTGCCGAGTGTCTGCTGGGAGTAATCCAC

AGCTCACCCAAGACAAGAGAAT
AGCTCACACCACGCCAAGAAAC
```

FIG. 21

SEQUENCE LISTING

```
<160> NUMBER OF SEQ ID NOS: 12

<210> SEQ ID NO 1
<211> LENGTH: 13728
<212> TYPE: DNA
<213> ORGANISM: Homo sapiens
<220> FEATURE:
<221> NAME/KEY: misc_feature
<222> LOCATION: (1)..(13728)
<223> OTHER INFORMATION: Human KCVN2 (full nucleotide sequence)
```

```
<400> SEQUENCE: 1
gccctaaaaa cgtcttccta ccattcctgg aattctacct tgaaacatgt ctctatcctt      60
taagagaaag ggaggagata aaaggagag agagaagctg aagctgactc aaagatccga      120
ctggacctga acagtgcccc agggagaatc catttgaaaa aaaaaaaaaa atgtgatcat      180
gtgaatggac aagaaggaga tggctttaga tcttatatgc tctaaacgaa gagttacgct      240
gagagggaaa ctgacttgtc atgaagtcag ctttgttccg ttgctatgtg tcatccctgc      300
taatggtgag tttacctagg gcagaggcta ccatctcaac catgaagctg aagacacagg      360
catccgtatt ctatagctaa ttcagttgat ttcatctcag cacacataca ctgagcgctt      420
cctaagagcg aggttgaccg acatttttat tagcaataat ctctgccttc ttctgattac      480
ctagagattt aagaccacat aatcatcctc tacctcacag ggtcaaggga gtggggagg      540 aaatgggcta agaggttcta aatccctcct aacacttgct tcttccaaat cagcaagatt      600
agagcagtca acagctgact gcgttcagac cctgcaggct gggctggcct gcccaggacc      660
tgagaagggg cagctccggt ggcaatgtct gagcccctag ctgtgctggt ccgggctggc      720
ctctctaaga cagtgcaggc cacgtgatcc atcctcctag aggcagtgag caggtgaggg      780 accccctacca cagccaggag gaaaaagcta ggcgtccact ttccgcagcc atgctcaaac      840
agagtgagag gagacggtcc tggagctaca ggccctggaa cacgacggag aatgagggca      900
gccaacaccg caggagcatt tgctccctgg gtgcccgttc cggctcccag ccagcatcc      960 acggctggac agagggcaac tataactact acatcgagga agacgaagac ggcgaggagg     1020
aggaccagtg gaaggacgac ctggcagaag aggaccagca ggcaggggag gtcaccaccg     1080
ccaagcccga gggccccagc gaccctccgg ccctgctgtc cacgctgaat gtgaacgtgg     1140
gtggccacac ctaccagctg gactactgcg agctggccgg cttccccaag acgcgcctag     1200
gtcgcctggc cacctccacc agccgcagcc gccagctaag cctgtgcgac gactacgagg     1260
agcagacaga cgaatacttc ttcgaccgcg acccggccgt cttccagctg gtctacaatt     1320
tctacctgtc cggggtgctg ctggtgctcg acgggctgtg tccgcgccgc ttcctggagg     1380
agctgggcta ctggggcgtg cggctcaagt acacgccacg ctgctgccgc atctgcttcg     1440
aggagcggcg cgacgagctg agcgaacggc tcaagatcca gcacgagctg cgcgcgcagg     1500
cgcaggtcga ggaggcggag gaactcttcc gcgacatgcg cttctacggc ccgcagcggc     1560
gccgcctctg gaacctcatg gagaagccat tctcctcggt ggccgccaag gccatcgggg     1620
tggcctccag caccttcgtg ctcgtctccg tggtggcgct ggcgctcaac accgtggagg     1680
agatgcagca gcactcgggg cagggcgagg gcggcccaga cctgcggccc atcctggagc     1740
acgtggagat gctgtgcatg ggcttcttca cgctcgagta cctgctgcgc ctagcctcca     1800
cgcccgacct gaggcgcttc gcgcgcagcg ccctcaacct ggtggacctg gtggccatcc     1860
tgccgctcta ccttcagctg ctgctcgagt gcttcacggg cgagggccac caacgcggcc     1920
agacggtggg cagcgtgggt aaggtgggtc aggtgttgcg cgtcatgcgc tcatgcgca     1980 tcttccgcat cctcaagctg gcgcgccact ccaccggact gcgtgccttc ggcttcacgc     2040
tgcgccagtg ctaccagcag gtgggctgcc tgctgctctt catcgccatg gcatcttca     2100 cttttctctgc ggctgtctac tctgtggagc acgatgtgcc cagcaccaac ttcactacca     2160 tccccccactc ctggtggtgg gccgcggtga gtaccctttgc cctgggcttt ccatcctct     2220 tccccagccc agtgagctgc tcctccctcc cctggttatc agccaccagg ctttggcttc     2280
tgatcctcgt cttccccccc accccaaatc gccgcataca gctaacaaaa cggcgatgga     2340
```

```
tgtcaaaagt ggtggaaaga gaactcagca gatcagtaag taagtgaatt tgacttagtc   2400
gtagaaatct ccaaatctag atttcgtctt caaaccttta aaagacaggt tttaaagaag   2460
atgcgtcatc attactgtta tttaccagtt attgagcatc cagtgtcctg acaaagctta   2520
tctcattgtg gcatcacagc cttTgagatg gttatgacca ccattttttt ttaaggggac   2580
aagcagaaat ggcttcagtt tttgaaagaa actgtagatt tatacagaga aggaggtgag   2640
acttggctga accatgttga ctctaactga aatcccacca cctctggttc cacttaaatc   2700
tgagtgtgga aagaagcatc tcaaactgaa acttgctctg acttcactaa agttctttca   2760
ggaccctgta ttattgcccc attttacaga tagtgaaatt gaagtacaga gagttTgaat   2820
gtggactcac agctagaggt ggcaaagcca gaactgaaac tcagtcctgt ccatctccaa   2880
actccatgcc tttcccacac ccaagcacag tctctttcaa gttttagttc ttttgcatgc   2940
attgctgaat ttgtacagtt agtgtaacag ttatttTttg tcattgtttt ctttggcctt   3000
tgccttttta taacttgtgc tgtttactca aatatctgta ttttgagctg tggtagctga   3060
atccctggaa ataaatgtta atcaggtctt ctcagatcga tgaataagtc ggcatatatg   3120
aaggaaagaa ttgaatgtat ggtttcctta gttttctttt gaaaagtaga ttgtaatacc   3180
tttaaagaca ttaagcaaat ataactagtt ttcccatgtc agaaagtaga tattttcaac   3240
attgtgtatg tcataaccca tagtctggtg tgcacttctg agacaaacca acccaaggcc   3300
actgacagtg caatgcagca taatagaaga tttagaaaac ctgattctag tcccagacct   3360
gtcaataatt aaccatgacc ctgaataatt aactgtgaaa ccttaatccc tcacttccag   3420
tcctgctttc tcacctctaa aaggggaggc tggacatgta aaagtctgca gttcagtgag   3480
tcttccttcc cttgaaagca gggagctcat atgtatagag gatatgtgag ctttcttcag   3540
tggcaggatg atacgatgtt cttctgaatg agctaggcaa attctgcttc tctgatcata   3600
ttccaagtga tgaaaggtca tccctatagt agataaacca tgtgtacaga tgaggctcat   3660
ggttgatgat ttgtccccag caaatgacat ttactttggg gtgactaaag caggaaagca   3720
gaagagtaaa tccacatgct gatgatatga tacaacactt gagagtcaaa tttctattca   3780
tctaaacatc tttaaaggct agtgcatgaa ggcactggag ctagtacact ctctgatact   3840
acagtttgaa cccacaaaag ttttttcgac cttttgtata ttaacaaata ctttgataaa   3900
agttatgtta ctttcaaacg gatatggcta gagaaaaaat tttaattaaa ataaaacaca   3960
taaagaataa tgttactcag gttgtatttt taccagtaaa ttttttttgaa ctgaatacccc  4020 attgatctca cttaaatttc tgatctgttc aatgtacaat gaagtctaaa cctttcaaat   4080
tatctctttt tatgttaact ggcactatgt aactcaaaat caatgttttt cataaatttt   4140
acaaaaattg aatcaccagt ttttgccaat cataaatgtt accaattatt gctcttatct   4200
gtatgaattt ccttttgaag ccattatctc tatcagccac tattttcata ggcccaattt   4260
tgcacattcc aaccatccca tttacaaacc ttacccttta tcaatggtct ttgtccattt   4320
tattctgaaa attatttata ccagtaaaat tcgttacaaa ttagataaaa gactgatcat   4380
ctgtatttat ttctaaacta atctatgaaa acaatgggag caattgccct tgaatattct   4440
aagaccgctc tgttccccag gactgctatg ttattaatcc agttcttctc tgtacttcta   4500
actacactcc ataatacaga ctaaaggttc atattctcaa tagagcaaag agaaaagaac   4560
acattgaatt gatgtggaca aaatgtcttg tttccggtat gtagatgcaa agtgaaaaga   4620
aacaaaacat taggaccaat ttgtcatata acccacaaaa attcaccttaa ttcattcatt   4680
```

```
gaacagtaag ttttgagca cctccaatgt gcccagtagt attcttaaca ctagggatac   4740
agggtaggag aagaaaaaac aatcaagttt tttctcttct ggagcttaca ttctaatgga   4800
gaaagacaga taataaataa tttcaggtat tggcatagct tgtgtgggat aacaagattg   4860
agagtgattc aggcagtaga gtctgtcttt agtgggatag tcagagaagc ccttttggag   4920
aagatgacat tgagataaag tttgaaagat gaaaagagac tcatctaaat gcacctgact   4980
caacagatat gacaatctga gaagaggatt cctaaaagta actgatctag tggtttctaa   5040
gcattttatt aatcatgcat cttatttta aaaatttggg gcacataccc atgataaatg    5100
tgtatttatt tataaataaa ttagaagtta tttatttata aataaattag aagttatta    5160 taaataaatt agaagttatt tataaataaa ttagaagtta tttataaata aattagaagt   5220
tatttataaa taaattagaa gttatttata aataaattag aagttattta taaataaat    5280 agaagttatt tatttataaa taaattagaa gttatttatt tataaataaa ttagaagtta   5340
tttatttaca aattagaagt tatttattta caaattagaa gttatttata aattagaagt   5400
tatttataaa taaattagaa gttatttata aataaattag aagttattta taaataaatt   5460
agaagttatt tataaataaa ttagaagtta tttataaata agttatttat aaatagaagt   5520
tatttataaa taagttattt ataaatagaa gttatttata aataagttat ttataaatag   5580
aagttattta taaataagtt atttataaat aaaagttatt tataaataaa ttagaagtta   5640
tttataaata aattagaagt tatttattta taaattagaa gttatttatt tataaataaa   5700
ttagaagtta tttatttata aataaattag aagttcttta ttgccataat aacgatacat   5760
caccaaccac cctgaaattc aatggcttaa aacatcaagc gtttatttag ctcatgaatt   5820
taaaagtcag cgtatactct gatttcagct agaaggttct tctctttcat gaggctcttg   5880
ttactcattc acatgcctga tggtcaactg gcatgaaggg agagactagg ccacatgtct   5940
gcattcctct ggcagactcc agcagccaca tgtcgatggc tgtggcaaag aacaagagag   6000
agaatgcaag ccccatcatg caaacacttc ataagtttct tttcatggca tttgctcagc   6060
ccattggcca gagtaagtca catggccaag ctgcaagtca aagggcaggg caggttagcc   6120
cacccaccat aggagggcac tgcaaagtta tatggcaaac agcttagaca cagaaagatg   6180
taaagaatta gttccaataa tgcaatcttt ctcctgcagt aatatattac tgctcaaata   6240
tattacacat atcagaaagt atacactcac aaattgaaac tttaaagatg agataaagaa   6300
aaatataatt ggcattttat ttcaccattc tggggctgta tcctttgtga aatatgcatc   6360
ccacattaca gagagtttct cttatccatt cttttatgta ttttaatac tttcagacaa    6420 caccaaatct gacttgcttt taataatctt tcttctctct atgccaagga tcctgcaaac   6480
tttctctgta attcaactca aggatttaag aaaaatacag tagttttcat tactgtgaat   6540
tctcctgcag ctgcaaaaca aatccctcct ggacacttat gtctacaaat gctcatgtat   6600
taggatgtag gatagacctg tcttttcat ctgtcaaatg gaggtattt gtgagcacta    6660 atgtaatagg aaacatatgt aaactgctag cctatagtaa gtctgcaata aatagaagct   6720
accataactg actagttgat agtctttgtc acatggaagc aataaccttt gcttctacat   6780
tcatttggga agaaaataaa acagaaatga ttcttttct actgaggaaa agaaagaacc    6840
tataaaacat acgagaaggt cagctgttcc ctcatgggag aacttctgag agtccagata   6900
aacaggccca cgcctaaagc agctccagcc atcttgggc tctctggatt gcctgggggt    6960
aggaaatgca cggcacagct aaacaagaac aatgggctct atgatgaagc tgtaatcatt   7020
ggcctcctgt gtgggtatgg tttttttctt ttacttttt tttttttta gcctcaacat     7080
```

```
atgaccacat ttttttttct tatttttttt ttgccggggg ttgggggtg gagggcatgg      7140 gtatgttttc aagtagaaaa gagtaagtag actttgaatg aaccatttcc ttctgagttt      7200
tccagggcaa gttaaagctg tagaaaccaa acaggaaact acggcatgaa ctcactcctt      7260
caaaaactaa cttctcaaaa agaaaattta tctctagttg aggcaccatt ttgtcccaga      7320
gaccttgctc ccatctttct ttccctaagg tatgttttca ttaccttgcc aataggtggc      7380
acttacaaga tcactgaaat tattttattt ttgttcattg attgctttga ggaaacccat      7440
ttgaaaaata aattaggttg cagtcaggaa aatagatacc aaggtgaata tttcaaacag      7500
ggaatttaat acaaggaaat agatagttgt tagaagacta gaagaagaaa aaaagaaga      7560 ctggaaaagc agaaagagaa aactgagata atccagagat tggtaattgc agggagtagc      7620 tattggcct agaattggga gaataaatgg gaaaaggtgt tgccaccaga agctaagagt      7680
ccacaggagg ggcctctgtg tagctgttgc aaggactcct aaattggcac catgaggctg      7740
atgccaggaa tgccaaaaaa tgcctgaacc atagctattg gctgcaattg gaggaatgaa      7800
ggcagaaacc agaggcagga ttagagaccc ttatgtcctc ataccatctt ccagtctctc      7860
ataggcagaa cataactaga agacagtggg caagagaatc tgggaaatgt agtttgcaga      7920
ctcccagttc tggaattata aaataaaata cagaagggtg tcaggcttgg gactaagaga      7980
caacatataa atatctggca cagaaagtaa tagagttcta cctccttcag aagtagcaca      8040
ggagctatag acggggtaaa ggctcttagg cattgttact acttttatc ttatggattc      8100 ccaattttgg agtggtctcc ttttatgtct taaagtatg ttcctcattt tagccaatat      8160
gatgtgagtg gaacatgaca gcatcattga gggcacggag aaatgcaggg aagctgaggg      8220
tgtggacagc atcattattg cgcacctttc tgtggataga ttaatagatc tcaaacttac      8280
atttgtggct ttgctttagc tgtgcacacc taccgcttat tgtaccactt acaaacatgt      8340
cagaactgta atatacagat gagggttgtt attatcctga aggtagtcac ccatgacctc      8400
attctaacag tgattccact aatcaagaca ttctttgaat tccactgagg aattaccttc      8460
agagtttgtg acacatccac ttgttttctag gttgttaaat ctttgtcttt ttaaggctac      8520
attcagtatt ttaaaatagt taagacactt tagtttaaga tcgacactta gagtaaacca      8580
tcaaggtgga tatgaccgct tgctgctact gaatctactg tgcagactat aattcaaaag      8640
aggaattcca aatatacttg ttgcaataat agcatgagta agtacagcct ttgaagctgg      8700
atcctttgaa ggacaacacg tattgaggct tataataatt ttatccaaaa aagatccatc      8760
ttcaccacct ctaattcctt tggaaaacag aaagagtgtt attttgaaaa ataagtttta      8820
ttccctagga tcataaattc ctgaatgcat ggactactgg gtgccaagat tgattccatt      8880
ccttgttcat tatgagggaa acaaacttgt cttgttaaat gagaaatcca agtattctca      8940
agttttggag aaaaatttga tgcttatcct cataatatat ggcaggccag gatttgttgt      9000
ttagtgagta aactgccagg ggaaggtcac attctggctt tgggacccaa ggctaaggaa      9060
agtatgtacg tttacagcag aatggttaag cttccagttt gcagagttgc tgagctagcc      9120
agttttcttc agtatattaa gatggattgc ggaaattttg gtcacatttc caacccaac      9180 tcctgctaat gtgacaactc attctgtgag gtcacttggg tcagtctggg gccttcagct      9240
tttaattccc atctagggag aaatggcttg gcctatggaa tgtggaaaaa agttcccca      9300 aagccaagga atcctgagtt cctcctggag ccaaggaaca agaaacagat cacttgttga      9360
gtcaaattat tcacgaaata gacaacatat aaattaactg tacattttca acaaattatt      9420
```

```
ggggaccagt cacacatagc ctcctagcag aagagatctg ttctctaaaa atagagattg    9480
aagatataca aaaatatttg gatcatatta tacacatcag atatttattc ttctttaagc    9540
caattctctt tgcttttgac ttttcactca aagttcagcc aaaaaaaaaa gaagtttggc    9600
ttaagggtga agcaaagcca gtgtgcagaa tgatcaaaag ttgaaaataa gcagtttatc    9660
ttaattattt tcttcctcag tgtcttccta ctctctccca tccccgccat cctgaaccct    9720
taagtgactt gtttcctcca aggcctctgc attggacttc cgtggatgtc tcatgttcta    9780
aaccagggt ccccaatccc gggctgtgga gtggtacttg tctgtggcct gttaggaacc    9840
cggccacaca gcaggagatg agtggagggc catcaatcat taccgcctaa gttctgcctc    9900
ctgtcagatc aaccacagcg ttagattctc ataggagtgg gaaccctatt gttaactgcg    9960
catgggaggg atctaggttg cttgctcctt atgagaatct aactaatacc tgacaacctg   10020
agatggagca gtttcatccc gaaaccatcc cctcccccaa ccccgtccat gggaaaaatg   10080
gtcgtccaca aaaccggtcc ctggtgccaa agaggttggg gaccgctgtt ctaaactacc   10140
ccttcctgtc actcactcct aaatccaaac tcccttaggg cctcctccag ggaaggttga   10200
ctaaactttc atccagaggt gtgagtcatg gtgttagtga caaatgaaag ctattgttca   10260
gctcacacaa ctggagagag atcagcctgg ggttctttga cttttggtgt ggtcaatgac   10320
aagaaacaca cacccggaca caggaagggg aacatcacac accagggcct gttgtggggt   10380
gggggagggg ggaggggtag catttggaga tatacctaac gttaaatgac aagttactgg   10440
gtgcagcaca ccaacatggc acatgtatac atatgtaact aacctgcacg ttgtgcacat   10500
gtaccctaga acttaaataa aaaaaagaca caccccactca tgcaaccaag aggactttga   10560
gattaaccca caatctcact ttatcactgc ctcacatcac cccttggtcc agaagttggg   10620
agaaggatat tctctactgg agccagaggg cagagtcagg gaggagcttg tttccacagc   10680
ctgagggtct gataagcata acgtatatag agttgctggt gtagaatgca ctcaataaat   10740
gttggtcttt gcctcttctc agtggaggcc agcttcagca tgggggaccc tgggattgca   10800
tacatgatat atatataata atattattgc ttacacaccc tgtgccaggc actccttcaa   10860
ttcctataac aactctgtga ggtagatacc acacatttca aaagtagaaa ctgaggccaa   10920
gagaatttag gtgatctgcc caacttattc agctgggaag tggattcaga cccacaagtc   10980
tactgtagtc cgtttccttc agcttatcta caccacatta cctctcttgg atgcctgctt   11040
gtattttgac tctgcagaaa aaggctgcat gacctctcac aagagacagg gcagtgagtg   11100
acaggaggtg catcatcagc ctcaaaaagg aggcataccc ttccttttt cgtgggctgg   11160
atggagctgt ggttctcatc agtgccctca gttttgtgca gctggctcac ttctccattt   11220
cattctaatc agtcaactgc actattccag gttcaaacta accttacat catcaaaaca   11280
aaaatattta cactgctaag ctaacggcca cctcagcacg gatcaacaag atgaccatat   11340
gctttactgc cgtctgctgg aaaattatgg caacaactac ccaaatacac aaagcaaaga   11400
gtgcccccct ggagtagtgc aacgcaaaaa tgtttacaac tgtgaccaac agctctgctt   11460
aaaaggcttc tagtaattta gccaatactc tggggatcag agggagtaca tgaggcataa   11520
aaaacagtcc ccaaggaatt ttcacagggt tttctctggt aactgataac tagtcccatg   11580
gtatctgcat tttaaaacag aagcttgtta acctaaataa gtctccaatt agtgggattt   11640
aaatcagtat gacaagagta atgggaagta tttcatgcag gggtgaacat attttttggtg   11700
agtgatgtct tacaaaagtc cctttacaaa ataatgagag tgtttctcca gacatctgca   11760
attaaagcac cttcacataa agtctctcat ttgaactacg taacaacttt gaaaagtgtt   11820
```

```
ataactgtct tcattttaaa gatgagagga agacaatgga ggagtttcat gccttttgta    11880
tgcctggtac tgtgttcagt gctttatatt cattttctta tttagccttc acaagaatcc    11940
taagagttag atggttttct cctgttttaa ataaaaaaaa aaaaaagaa aaaaagaaaa     12000 agagagagag agagtctgaa ggttttgccc caggtcactc aactggaaag gttcagagtc    12060
aggacttgaa cccaggtctg actgttctaa gcccaagatt tttccaatac atacagtgta    12120
caggcaaacc cagggacctg ctttcctgaa tctggtgcca gctgagttag ggaggcaaag    12180
atcatttact gagcacgttc tacatcaggt acttaacata ctattttaaa tgctctttac    12240
agcaaccatt tcaagtaggt attacctcct cctcccatat cttacattca aacatgcatg    12300
agtcgtagtc aggatttcag ccaaagtctt tcagctccat ccatagcttc tgttcttttc    12360
atgacacagg tcctagaggg agtcttcctg gtacctccta aagcaggctc cgtgggaagc    12420
cattacactt cccatgtgta cccacaggga ggacgcttcc ctgcttgctc ctctcccttt    12480
cttctcctcc ccgatcttag tgctaacaat tccatcctgc tttccttcct ctacaggtga    12540
gcatctccac cgtgggctac ggagacatgt acccagagac ccacctgggc aggttttttg    12600
ccttcctctg cattgctttt gggatcattc tcaacgggat gcccatttcc atcctctaca    12660
acaagttttc tgattactac agcaagctga aggcttatga gtataccacc atacgcaggg    12720
agaggggaga ggtgaacttc atgcagagag ccagaaagaa gatagctgag tgtttgcttg    12780
gaagcaaccc acagctcacc ccaagacaag agaattagta ttttatagga catgtggctg    12840
gtagattcca tgaacttcaa ggcttcattg ctctttttt aatcattatg attggcagca    12900
aaaggaaatg tgaagcagac atacacaaag gccatttcgt tcacaaagta ctgcctctag    12960
aaatactcat tttggcccaa actcagaatg tctcatagtt gctctgtgtt gtgtgaaaca    13020
tctgaccttc tcaatgacgt tgatattgaa aacctgaggg gagcaacagc ttagattttt    13080
cttgtagctt ctcgtggcat ctagctcaat aaatattttt ggacttgagt tgacttgaga    13140 aaatttttt tactttaaat ttttctaaaa ttcttaactt tccagaggga gggagggtta    13200
cagcagaaat tatacaagct ttggagttag accaacctta gtcagaatcc cagagctacc    13260
agctgtatgc ttttaggcaa gcgactctaa ccctttaagc ctcagtttct tcaactgtga    13320
aatgtaggca atacttaccc tgccaggctg agcaatatag tgagaccctg cctctacaaa    13380
aacttattaa gaattatctg ggtgtgctgg cccacacctg tagtcccagc tacttggaag    13440
actgaggtga gatcacttga gcccaggagt ttgaggttag agtaagctat aaccacatta    13500
ctgcactcca atctagatgg cagagtaaga ccctgcctca aataaataaa taaataaata    13560
aataaataaa accacctgcc ttgtaaaatg agtctgggga taacagatat gtgtaaacgc    13620
tcaataaatg ataggtatta aaattgttta agtggatgtt atctagtgaa atctctagac    13680
cagtggttct caaaggcaaa ttcattcctc agaggccagc taatgcct              13728
```

<210> SEQ ID NO 2
<211> LENGTH: 1638
<212> TYPE: DNA
<213> ORGANISM: Artificial Sequence
<220> FEATURE:
<223> OTHER INFORMATION: Synthetic: Codon Optimized hKCVN2 (nucleotide
      sequence)

<400> SEQUENCE: 2

```
atgctgaagc agagtgagag gaggaggtca tggagttatc gaccttggaa cacgactgaa     60
aacgaaggca gccagcatcg cagatccatt tgctccctgg gggcgcgcag tggctcacaa    120
```

```
gcgtccatcc acggctggac tgaaggaaat tataactact atatagagga ggacgaagac    180
ggagaggagg aagaccaatg gaaagatgat ctggcggagg aagatcagca agccggtgaa    240
gtgaccactg ctaaacccga aggaccatct gacccacctg cactcttgag cacattgaat    300
gtaaatgttg ggggtcacag ctaccaattg gattactgcg agcttgccgg gtttcccaag    360
actcggctcg gaaggctcgc aacatccaca agcaggtccc ggcaattgtc actgtgcgat    420
gactatgaag aacaaacaga cgagtatttc tttgacaggg acccggctgt cttccagttg    480
gtctataact tctatctgtc aggtgttctc ctcgttctcg atggcctgtg tcctcggcga    540
ttcttggaag aactcgggta ctgggggtg aggttgaaat ataccctcg gtgctgccgc    600 atttgttttg aggaaggcg agatgagctt tcagagcggt tgaagataca acacgaactt    660
agagcgcagg ctcaggtaga agaagctgaa gaattgtttc gagacatgag attttatggc    720
ccacagcgcc gccggctgtg aacctcatg gaaaagcctt tctcaagtgt cgccgccaag    780
gctattggcg ttgccagcag cactttcgta cttgtgagcg tagtggcact ggcattgaat    840
actgtagagg agatgcagca gcacagcgga cagggtgaag gggggcctga ccttcggcct    900
atcctcgaac atgtcgaaat gctctgcatg gggtttttca ccttggagta ccttcttcga    960
cttgcatcta cgccagactt gcggagattt gctaggagcg ctcttaacct ggttgacctc   1020
gtcgcgatcc tgccgttgta cctccagctg cttctcgagt gttttacagg tgagggtcac   1080
caacgcggcc agactgtcgg gagcgtcgga aaggttggtc aggttctgcg cgtcatgaga   1140
ttgatgagga tatttagaat cctcaaattg gctagacata gtactgggtt gcgcgcattc   1200
ggtttcaccc ttcgacagtg ctatcagcaa gttgggtgct tgctcttgtt catcgctatg   1260
ggaatcttca ctttttccgc cgccgtatat tccgtagaac atgacgttcc ctccaccaat   1320
tttacaacaa tcccgcatag ctggtggtgg gctgctgtct ccatctctac ggtcggctac   1380
ggcgacatgt accccgaaac gcacctcggt aggttcttcg catttctgtg catcgcgttt   1440
ggaatcattc ttaatggtat gcctatttca atactttaca ataaattctc cgattactac   1500
agtaaattga agcatacga gtatactacg attcggcgcg agagggcga agtaaatttc   1560 atgcagcgag caagaaaaaa aattgccgag tgtctgctgg ggagtaatcc acagctcaca   1620
ccacgccaag aaaactag                                                  1638
```

<210> SEQ ID NO 3
<211> LENGTH: 5971
<212> TYPE: DNA
<213> ORGANISM: Artificial Sequence
<220> FEATURE:
<223> OTHER INFORMATION: Synthetic: Complete DNA Sequence of Construct,
     pAAV_RK_KOZAK_hKCNV2_WPRE-SV40 FULL SEQUENCE

<400> SEQUENCE: 3

```
gatatcctta aggatccag atctgaattc gggccccaga agcctggtgg ttgtttgtcc    60
ttctcagggg aaaagtgagg cggccccttg gaggaagggg ccgggcagaa tgatctaatc   120
ggattccaag cagctcaggg gattgtcttt ttctagcacc ttcttgccac tcctaagcgt   180
cctccgtgac cccggctggg atttagcctg gtgctgtgtc agcccggtc tcccagggc    240 ttcccagtgg tccccaggaa ccctcgacag ggcccggtct ctctcgtcca gcaagggcag   300
ggacgggcca caggccaagg gcggtacgcc gccaccatgc tgaagcagag tgagaggagg   360
aggtcatgga gttatcgacc ttggaacacg actgaaaacg aaggcagcca gcatcgcaga   420
tccatttgct ccctgggggc gcgcagtggc tcacaagcgt ccatccacgg ctggactgaa   480
```

-continued

| | |
|---|---|
| ggaaattata actactatat agaggaggac gaagacggag aggaggaaga ccaatggaaa | 540 |
| gatgatctgg cggaggaaga tcagcaagcc ggtgaagtga ccactgctaa acccgaagga | 600 |
| ccatctgacc cacctgcact cttgagcaca ttgaatgtaa atgttggggg tcacagctac | 660 |
| caattggatt actgcgagct tgccgggttt cccaagactc ggctcggaag gctcgcaaca | 720 |
| tccacaagca ggtcccggca attgtcactg tgcgatgact atgaagaaca aacagacgag | 780 |
| tatttctttg acagggaccc ggctgtcttc cagttggtct ataacttcta tctgtcaggt | 840 |
| gttctcctcg ttctcgatgg cctgtgtcct cggcgattct tggaagaact cgggtactgg | 900 |
| ggggtgaggt tgaaatatac ccctcggtgc tgccgcattt gttttgagga aaggcgagat | 960 |
| gagctttcag agcggttgaa gatacaacac gaacttagag cgcaggctca ggtagaagaa | 1020 |
| gctgaagaat tgtttcgaga catgagattt tatggcccac agcgccgccg gctgtggaac | 1080 |
| ctcatggaaa agcctttctc aagtgtcgcc gccaaggcta ttggcgttgc cagcagcact | 1140 |
| ttcgtacttg tgagcgtagt ggcactggca ttgaatactg tagaggagat gcagcagcac | 1200 |
| agcggacagg gtgaaggggg gcctgacctt cggcctatcc tcgaacatgt cgaaatgctc | 1260 |
| tgcatggggt ttttcacctt ggagtacctt cttcgacttg catctacgcc agacttgcgg | 1320 |
| agatttgcta ggagcgctct taacctggtt gacctcgtcg cgatcctgcc gttgtacctc | 1380 |
| cagctgcttc tcgagtgttt tacaggtgag ggtcaccaac gcggcagac tgtcgggagc | 1440 |
| gtcggaaagg ttggtcaggt tctgcgcgtc atgagattga tgaggatatt tagaatcctc | 1500 |
| aaattggcta gacatagtac tggggttgcgc gcattcggtt tcacccttcg acagtgctat | 1560 |
| cagcaagttg ggtgcttgct cttgttcatc gctatgggaa tcttcacttt ttccgccgcc | 1620 |
| gtatattccg tagaacatga cgttccctcc accaattta caacaatccc gcatagctgg | 1680 |
| tggtgggctg ctgtctccat ctctacggtc ggctacggcg acatgtaccc cgaaacgcac | 1740 |
| ctcggtaggt tcttcgcatt tctgtgcatc gcgtttggaa tcattcttaa tggtatgcct | 1800 |
| atttcaatac tttacaataa attctccgat tactacagta aattgaaagc atacgagtat | 1860 |
| actacgattc ggcgcgagag gggcgaagta aatttcatgc agcgagcaag aaaaaaaatt | 1920 |
| gccgagtgtc tgctggggag taatccacag ctcacaccac gccaagaaaa ctagaagctt | 1980 |
| atcgataatc aacctctgga ttacaaaatt tgtgaaagat tgactggtat tcttaactat | 2040 |
| gttgctcctt ttacgctatg tggatacgct gctttaatgc ctttgtatca tgctattgct | 2100 |
| tcccgtatgg ctttcatttt ctcctccttg tataaatcct ggttgctgtc tctttatgag | 2160 |
| gagttgtggc ccgttgtcag gcaacgtggc gtggtgtgca ctgtgtttgc tgacgcaacc | 2220 |
| cccactggtt ggggcattgc caccacctgt cagctccttt ccggactttc gctttccccc | 2280 |
| ctccctattg ccacgcgga actcatcgcc gcctgcttg cccgctgctg acagggggct | 2340 |
| cggctgttgg gcactgacaa ttccgtggtg ttgtcgggga atcatcgtc ctttccttgg | 2400 |
| ctgctcgcct gtgttgccac ctggattctg cgcgggacgt ccttctgcta cgtcccttcg | 2460 |
| gccctcaatc cagcggacct tccttcccgc ggcctgctgc cggctctgcg gcctcttccg | 2520 |
| cgtcttcgcc ttcgccctca gacgagtcgg atctcccttt gggccgcctc cccgcatcga | 2580 |
| taccgtcgac ctcgacccgg gcggccgctt cgagcagaca tgataagata cattgatgag | 2640 |
| tttggacaaa ccacaactag aatgcagtga aaaaaatgct ttatttgtga atttgtgat | 2700 |
| gctattgctt tatttgtaac cattataagc tgcaataaac aagttgctag cctgcagact | 2760 |
| agttctagag atatcatctt cctagagcat ggctacgtag ataagtagca tggcgggtta | 2820 |

```
atcattaact acaaggaacc cctagtgatg gagttggcca ctccctctct gcgcgctcgc    2880
tcgctcactg aggccgggcg accaaaggtc gcccgacgcc cgggctttgc ccgggcggcc    2940
tcagtgagcg agcgagcgcg cagccttaat taacctaatt cactggccgt cgttttacaa    3000
cgtcgtgact gggaaaaccc tggcgttacc caacttaatc gccttgcagc acatcccccct   3060 ttcgccagct ggcgtaatag cgaagaggcc cgcaccgatc gcccttccca acagttgcgc    3120
agcctgaatg gcgaatggga cgcgccctgt agcggcgcat taagcgcggc gggtgtggtg    3180
gttacgcgca gcgtgaccgc tacacttgcc agcgccctag cgcccgctcc tttcgctttc    3240
ttcccttcct ttctcgccac gttcgccggc tttccccgtc aagctctaaa tcggggggctc    3300 cctttagggt tccgatttag tgctttacgg cacctcgacc ccaaaaaact tgattagggt    3360
gatggttcac gtagtgggcc atcgccctga tagacggttt ttcgcccttt gacgttggag    3420
tccacgttct ttaatagtgg actcttgttc caaactggaa caacactcaa ccctatctcg    3480
gtctattctt ttgatttata agggattttg ccgatttcgg cctattggtt aaaaaatgag    3540
ctgatttaac aaaaatttaa cgcgaatttt aacaaaatat taacgtttat aatttcaggt    3600
ggcatcttcc ggggaaatgt gcgcggaacc cctatttgtt tatttttcta atacattca    3660 aatatgtatc cgctcatgag acaataaccc tgataaatgc ttcaataata ttgaaaagg    3720 aagagtatga gtattcaaca tttccgtgtc gcccttattc cctttttgc ggcattttgc    3780 cttcctgttt ttgctcaccc agaaacgctg gtgaaagtaa aagatgctga agatcagttg    3840
ggtgcacgag tgggttacat cgaactggat ctcaatagtg gtaagatcct tgagagtttt    3900
cgccccgaag aacgttttcc aatgatgagc acttttaaag ttctgctatg tggcgcggta    3960
ttatcccgta ttgacgccgg gcaagagcaa ctcggtcgcc gcatacacta ttctcagaat    4020
gacttggttg agtactcacc agtcacagaa aagcatctta cggatggcat gacagtaaga    4080
gaattatgca gtgctgccat aaccatgagt gataacactg cggccaactt acttctgaca    4140
acgatcggag gaccgaagga gctaaccgct tttttgcaca acatggggga tcatgtaact    4200
cgccttgatc gttgggaacc ggagctgaat gaagccatac caaacgacga gcgtgacacc    4260
acgatgcctg tagtaatggt aacaacgttg cgcaaactat taactggcga actacttact    4320
ctagcttccc ggcaacaatt aatagactgg atggaggcgg ataaagttgc aggaccactt    4380
ctgcgctcgg cccttccggc tggctggttt attgctgata aatctggagc cggtgagcgt    4440
gggtctcgcg gtatcattgc agcactgggg ccagatggta agccctcccg tatcgtagtt    4500
atctacacga cggggagtca ggcaactatg gatgaacgaa atagacagat cgctgagata    4560
ggtgcctcac tgattaagca ttggtaactg tcagaccaag tttactcata tatactttag    4620
attgatttaa aacttcattt ttaatttaaa aggatctagg tgaagatcct ttttgataat    4680
ctcatgacca aaatccctta acgtgagttt tcgttccact gagcgtcaga ccccgtagaa    4740
aagatcaaag gatcttcttg agatcctttt tttctgcgcg taatctgctg cttgcaaaca    4800
aaaaaaccac cgctaccagc ggtggtttgt ttgccggatc aagagctacc aactcttttt    4860
ccgaaggtaa ctggcttcag cagagcgcag ataccaaata ctgtccttct agtgtagccg    4920
tagttaggcc accacttcaa gaactctgta gcaccgccta catacctcgc tctgctaatc    4980
ctgttaccag tggctgctgc cagtggcgat aagtcgtgtc ttaccgggtt ggactcaaga    5040
cgatagttac cggataaggc gcagcggtcg ggctgaacgg ggggttcgtg cacacagccc    5100
agcttggagc gaacgaccta caccgaactg agatacctac agcgtgagct atgagaaagc    5160
gccacgcttc ccgaagggag aaaggcggac aggtatccgg taagcggcag ggtcggaaca    5220
```

```
ggagagcgca cgagggagct tccaggggga aacgcctggt atctttatag tcctgtcggg    5280
tttcgccacc tctgacttga gcgtcgattt ttgtgatgct cgtcaggggg gcggagccta    5340
tggaaaaacg ccagcaacgc ggcctttttα cggttcctgg ccttttgctg cggttttgct    5400
cacatgttct ttcctgcgtt atcccctgat tctgtggata accgtattac cgcctttgag    5460
tgagctgata ccgctcgccg cagccgaacg accgagcgca gcgagtcagt gagcgaggaa    5520
gcggaagagc gcccaatacg caaaccgcct ctccccgcgc gttggccgat tcattaatgc    5580
agctggcacg acaggtttcc cgactggaaa gcgggcagtg agcgcaacgc aattaatgtg    5640
agttagctca ctcattaggc accccaggct ttacacttta tgcttccggc tcgtatgttg    5700
tgtggaattg tgagcggata acaatttcac acaggaaaca gctatgacca tgattacgcc    5760
agatttaatt aaggctgcgc gctcgctcgc tcactgaggc cgcccgggca aagcccgggc    5820
gtcgggcgac ctttggtcgc ccggcctcag tgagcgagcg agcgcgcaga gagggagtgg    5880
ccaactccat cactagggt tccttgtagt taatgattaa cccgccatgc tacttatcta    5940
cgtagccatg ctctaggaag atcggaattc g                                  5971

<210> SEQ ID NO 4
<211> LENGTH: 130
<212> TYPE: DNA
<213> ORGANISM: Artificial Sequence
<220> FEATURE:
<223> OTHER INFORMATION: Synthetic: 5 ITR nucleotide sequence

<400> SEQUENCE: 4
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct                                                           130

<210> SEQ ID NO 5
<211> LENGTH: 130
<212> TYPE: DNA
<213> ORGANISM: Artificial Sequence
<220> FEATURE:
<223> OTHER INFORMATION: Synthetic: 3 ITR nucleotide sequence

<400> SEQUENCE: 5
aggaacccct agtgatggag ttggccactc cctctctgcg cgctcgctcg ctcactgagg     60
ccgggcgacc aaaggtcgcc cgacgcccgg gctttgcccg gcggcctca gtgagcgagc    120 gagcgcgcag                                                          130

<210> SEQ ID NO 6
<211> LENGTH: 297
<212> TYPE: DNA
<213> ORGANISM: Artificial Sequence
<220> FEATURE:
<223> OTHER INFORMATION: Synthetic: RK Promoter

<400> SEQUENCE: 6 gggcccaga agcctggtgg ttgtttgtcc ttctcagggg aaaagtgagg cggccccttg      60
gaggaagggg ccgggcagaa tgatctaatc ggattccaag cagctcaggg gattgtcttt    120
ttctagcacc ttcttgccac tcctaagcgt cctccgtgac cccggctggg atttagcctg    180
gtgctgtgtc agcccggtc tcccaggggc ttcccagtgg tccccaggaa ccctcgacag    240
ggcccggtct ctctcgtcca gcaagggcag ggacgggcca caggccaagg gcggtac      297
```

<210> SEQ ID NO 7
<211> LENGTH: 583
<212> TYPE: DNA
<213> ORGANISM: Human cytomegalovirus
<220> FEATURE:
<221> NAME/KEY: misc_feature
<222> LOCATION: (1)..(583)
<223> OTHER INFORMATION: CMV Promoter nucleotide sequence

<400> SEQUENCE: 7

| | | | | | |
|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggag | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catggtgatg | cggttttggc | agtacatcaa | tgggcgtgga | tagcggtttg | actcacgggg | 420 |
| atttccaagt | ctccacccca | ttgacgtcaa | tgggagtttg | ttttggcacc | aaaatcaacg | 480 |
| ggactttcca | aaatgtcgta | acaactccgc | cccattgacg | caaatgggcg | gtaggcgtgt | 540 |
| acggtgggag | gtctatataa | gcagagctgg | tttagtgaac | cgt | | 583 |

<210> SEQ ID NO 8
<211> LENGTH: 9
<212> TYPE: DNA
<213> ORGANISM: Artificial Sequence
<220> FEATURE:
<223> OTHER INFORMATION: Synthetic: KOZAK nucleotide seq

<400> SEQUENCE: 8 gccgccacc                                                                    9

<210> SEQ ID NO 9
<211> LENGTH: 542
<212> TYPE: DNA
<213> ORGANISM: Woodchuck Hepatitis Virus
<220> FEATURE:
<221> NAME/KEY: misc_feature
<222> LOCATION: (1)..(542)
<223> OTHER INFORMATION: Woodchuck Hepatitis Virus (WHP)
      Posttranscriptional Regulatory Element (WPRE)

<400> SEQUENCE: 9

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aacccccact | 240 |
| ggttggggca | ttgccaccac | ctgtcagctc | ctttccggga | ctttcgcttt | ccccctccct | 300 |
| attgccacgg | cggaactcat | cgccgcctgc | cttgcccgct | gctggacagg | ggctcggctg | 360 |
| ttgggcactg | acaattccgt | ggtgttgtcg | gggaaatcat | cgtcctttcc | ttggctgctc | 420 |
| gcctgtgttg | ccacctggat | tctgcgcggg | acgtccttct | gctacgtccc | ttcggccctc | 480 |
| aatccagcgg | accttccttc | ccgcggcctg | ctgccggctc | tgcggcctct | tccgcgtctt | 540 |
| cg | | | | | | 542 |

<210> SEQ ID NO 10

-continued

<211> LENGTH: 215
<212> TYPE: DNA
<213> ORGANISM: Bos taurus
<220> FEATURE:
<221> NAME/KEY: misc_feature
<222> LOCATION: (1)..(215)
<223> OTHER INFORMATION: Bovine growth hormone polyadenylation (BGH)
      poly(A)

<400> SEQUENCE: 10
gcctcgactg tgccttctag ttgccagcca tctgttgttt gcccctcccc cgtgccttcc     60
ttgaccctgg aaggtgccac tcccactgtc ctttcctaat aaaatgagga aattgcatcg    120
cattgtctga gtaggtgtca ttctattctg gggggtgggg tggggcagga cagcaagggg    180
gaggattggg aagacaatag caggcatgct gggga                               215

<210> SEQ ID NO 11
<211> LENGTH: 545
<212> TYPE: PRT
<213> ORGANISM: Homo sapiens
<220> FEATURE:
<221> NAME/KEY: misc_feature
<222> LOCATION: (1)..(545)
<223> OTHER INFORMATION: KCVN2 Amino Acid Sequence

<400> SEQUENCE: 11

Met Leu Lys Gln Ser Glu Arg Arg Ser Trp Ser Tyr Arg Pro Trp
1               5                   10                  15

Asn Thr Thr Glu Asn Glu Gly Ser Gln His Arg Arg Ser Ile Cys Ser
            20                  25                  30

Leu Gly Ala Arg Ser Gly Ser Gln Ala Ser Ile His Gly Trp Thr Glu
        35                  40                  45

Gly Asn Tyr Asn Tyr Tyr Ile Glu Glu Asp Glu Asp Gly Glu Glu Glu
    50                  55                  60

Asp Gln Trp Lys Asp Asp Leu Ala Glu Asp Gln Gln Ala Gly Glu
65                  70                  75                  80

Val Thr Thr Ala Lys Pro Glu Gly Pro Ser Asp Pro Ala Leu Leu
                85                  90                  95

Ser Thr Leu Asn Val Asn Val Gly Gly His Ser Tyr Gln Leu Asp Tyr
            100                 105                 110

Cys Glu Leu Ala Gly Phe Pro Lys Thr Arg Leu Gly Arg Leu Ala Thr
        115                 120                 125

Ser Thr Ser Arg Ser Arg Gln Leu Ser Leu Cys Asp Asp Tyr Glu Glu
    130                 135                 140

Gln Thr Asp Glu Tyr Phe Phe Asp Arg Asp Pro Ala Val Phe Gln Leu
145                 150                 155                 160

Val Tyr Asn Phe Tyr Leu Ser Gly Val Leu Leu Val Leu Asp Gly Leu
                165                 170                 175

Cys Pro Arg Arg Phe Leu Glu Glu Leu Gly Tyr Trp Gly Val Arg Leu
            180                 185                 190

Lys Tyr Thr Pro Arg Cys Cys Arg Ile Cys Phe Glu Glu Arg Arg Asp
        195                 200                 205

Glu Leu Ser Glu Arg Leu Lys Ile Gln His Glu Leu Arg Ala Gln Ala
    210                 215                 220

Gln Val Glu Glu Ala Glu Glu Leu Phe Arg Asp Met Arg Phe Tyr Gly
225                 230                 235                 240

Pro Gln Arg Arg Arg Leu Trp Asn Leu Met Glu Lys Pro Phe Ser Ser
                245                 250                 255

-continued

```
Val Ala Ala Lys Ala Ile Gly Val Ala Ser Ser Thr Phe Val Leu Val
                260                 265                 270

Ser Val Val Ala Leu Ala Leu Asn Thr Val Glu Glu Met Gln Gln His
            275                 280                 285

Ser Gly Gln Gly Glu Gly Pro Asp Leu Arg Pro Ile Leu Glu His
        290                 295                 300

Val Glu Met Leu Cys Met Gly Phe Phe Thr Leu Glu Tyr Leu Leu Arg
305                 310                 315                 320

Leu Ala Ser Thr Pro Asp Leu Arg Arg Phe Ala Arg Ser Ala Leu Asn
                325                 330                 335

Leu Val Asp Leu Val Ala Ile Leu Pro Leu Tyr Leu Gln Leu Leu Leu
            340                 345                 350

Glu Cys Phe Thr Gly Glu Gly His Gln Arg Gly Gln Thr Val Gly Ser
        355                 360                 365

Val Gly Lys Val Gly Gln Val Leu Arg Val Met Arg Leu Met Arg Ile
    370                 375                 380

Phe Arg Ile Leu Lys Leu Ala Arg His Ser Thr Gly Leu Arg Ala Phe
385                 390                 395                 400

Gly Phe Thr Leu Arg Gln Cys Tyr Gln Gln Val Gly Cys Leu Leu Leu
                405                 410                 415

Phe Ile Ala Met Gly Ile Phe Thr Phe Ser Ala Ala Val Tyr Ser Val
            420                 425                 430

Glu His Asp Val Pro Ser Thr Asn Phe Thr Thr Ile Pro His Ser Trp
        435                 440                 445

Trp Trp Ala Ala Val Ser Ile Ser Thr Val Gly Tyr Gly Asp Met Tyr
    450                 455                 460

Pro Glu Thr His Leu Gly Arg Phe Phe Ala Phe Leu Cys Ile Ala Phe
465                 470                 475                 480

Gly Ile Ile Leu Asn Gly Met Pro Ile Ser Ile Leu Tyr Asn Lys Phe
                485                 490                 495

Ser Asp Tyr Tyr Ser Lys Leu Lys Ala Tyr Glu Tyr Thr Thr Ile Arg
            500                 505                 510

Arg Glu Arg Gly Glu Val Asn Phe Met Gln Arg Ala Arg Lys Lys Ile
        515                 520                 525

Ala Glu Cys Leu Leu Gly Ser Asn Pro Gln Leu Thr Pro Arg Gln Glu
    530                 535                 540

Asn
545
```

```
<210> SEQ ID NO 12
<211> LENGTH: 1638
<212> TYPE: DNA
<213> ORGANISM: Homo sapiens
<220> FEATURE:
<221> NAME/KEY: misc_feature
<222> LOCATION: (1)..(1638)
<223> OTHER INFORMATION: Human KCVN2 (coding region nucleotide sequence)

<400> SEQUENCE: 12
atgctcaaac agagtgagag gagacggtcc tggagctaca ggccctggaa cacgacggag    60
aatgagggca gccaacaccg caggagcatt tgctccctgg gtgcccgttc cggctcccag   120
gccagcatcc acggctggac agagggcaac tataactact acatcgagga agacgaagac   180
ggcgaggagg aggaccagtg gaaggacgac ctggcagaag aggaccagca ggcagggag    240 gtcaccaccg ccaagcccga gggccccagc gaccctccgg ccctgctgtc cacgctgaat   300
```

```
gtgaacgtgg gtggccacag ctaccagctg gactactgcg agctggccgg cttccccaag      360
acgcgcctag gtcgcctggc cacctccacc agccgcagcc gccagctaag cctgtgcgac      420
gactacgagg agcagacaga cgaatacttc ttcgaccgcg acccggccgt cttccagctg      480
gtctacaatt tctacctgtc cggggtgctg ctggtgctcg acgggctgtg tccgcgccgc      540
ttcctggagg agctgggcta ctggggcgtg cggctcaagt acacgccacg ctgctgccgc      600
atctgcttcg aggagcggcg cgacgagctg agcgaacggc tcaagatcca gcacgagctg      660
cgcgcgcagg cgcaggtcga ggaggcggag gaactcttcc gcgacatgcg cttctacggc      720
ccgcagcggc gccgcctctg gaacctcatg gagaagccat tctcctcggt ggccgccaag      780
gccatcgggg tggcctccag caccttcgtg ctcgtctccg tggtggcgct ggcgctcaac      840
accgtggagg agatgcagca gcactcgggg cagggcgagg gcggcccaga cctgcggccc      900
atcctggagc acgtggagat gctgtgcatg ggcttcttca cgctcgagta cctgctgcgc      960
ctagcctcca cgcccgacct gaggcgcttc gcgcgcagcg ccctcaacct ggtggacctg     1020
gtggccatcc tgccgctcta ccttcagctg ctgctcgagt gcttcacggg cgagggccac     1080
caacgcggcc agacggtggg cagcgtgggt aaggtgggtc aggtgttgcg cgtcatgcgc     1140
ctcatgcgca tcttccgcat cctcaagctg gcgcgccact ccaccggact gcgtgccttc     1200
ggcttcacgc tgcgccagtg ctaccagcag gtgggctgcc tgctgctctt catcgccatg     1260
ggcatcttca ctttctctgc ggctgtctac tctgtggagc acgatgtgcc cagcaccaac     1320
ttcactacca tcccccactc ctggtggtgg gccgcggtga gcatctccac cgtgggctac     1380
ggagacatgt acccagagac ccacctgggc aggtttttg ccttcctctg cattgctttt      1440
gggatcattc tcaacgggat gcccatttcc atcctctaca acaagtttc tgattactac      1500 agcaagctga aggcttatga gtataccacc atacgcaggg agagggggaga ggtgaacttc     1560 atgcagagag ccagaaagaa gatagctgag tgtttgcttg gaagcaaccc acagctcacc     1620
ccaagacaag agaattag                                                   1638
```

KCNV2 VARIANTS AND THEIR USE

CROSS REFERENCE TO RELATED APPLICATIONS

This application claims priority to U.S. Provisional Application No. 63/191,106 filed May 20, 2021, incorporated by reference in its entirety.

FIELD OF THE DISCLOSURE

This relates to novel nucleotide and protein sequences, such as KCNV2 sequences, as well as recombinant nucleic acid molecules and vectors, and related methods of use to treat a retinal disorder, such as cone dystrophy, in a subject.

BACKGROUND

Cone dystrophy, for example but not limited to, cone dystrophy with supernormal rod response [CDSRR], is an autosomal recessive disorder that may be characterized by, e.g., poor visual acuity, vision loss, sensitivity to light, poor color vision, nystagmus and strabismus, among others. Visual difficulties begin in early childhood with acuity of, e.g., 20/100 or less by the second decade of life. Patients may later develop night blindness and many or most patients may also develop myopia. No specific treatment is available to either reduce or prevent the progression of visual loss, leaving patients with a poor prognosis and declining quality of life as they age. Thus, there is a need to identify therapies.

SUMMARY

We disclose novel recombinant nucleic acid molecules, proteins, vectors, and related methods of use to treat cone dystrophy with supernormal rod response [CDSRR] (Retinal cone dystrophy 3B, OMIM 610356) and related pathologies indicated by KCNV2. CDSRR is a rare, recessive, and inherited retinopathy that is characterized by poor visual acuity (due to central scotoma), photophobia, severe color vision deficits, and occasionally, nystagmus and strabismus are also present. In some patients, the fundus appears normal but foveal or parafoveal atrophy, a macular bull's eye, hyperfluorescence anomalies, and a generalized fine pigmentary retinopathy have been reported. There may be some temporal pallor in the optic nerves.

Disclosed herein are nucleic acids, transcriptional control units (TCUs), optimized gene sequences, expression constructs, and vectors for expressing genes in retinal cells, including but not limited to, cone photoreceptors and/or rod photoreceptors.

Disclosed herein are modified KCNV2 genes containing nucleic acid replacements in an unmodified KCNV2 gene, wherein the nucleic acid replacement can be one or more of those demonstrated by alignment of the human KCNV2 gene with the codon-optimized version represented by SEQ ID NO 2.

Also provided are nucleic acids, transcriptional control units (TCUs), optimized gene sequences, expression constructs, and vectors for expressing genes in photoreceptors, e.g, cone photoreceptors and/or rod photoreceptors.

Also provided are vectors, such as an adeno-associated virus (AAV) vector, containing the nucleic acid molecules, as well as isolated Kv8.2 proteins encoded by the nucleic acid molecules.

Also provided are expression constructs, comprising a variant human KCNV2 gene under control of TCUs. In a variation, the KCNV2 is under the control of a promoter optimized for expressing genes in photoreceptors, e.g., cone photoreceptors or rod photoreceptors. In a variation, the variant human KCNV2 gene may be under the control of the rhodopsin kinase (RK) promoter.

Accordingly, in one variation we provide:

A promoter capable of directing expression of the KCNV2 gene. In a variation, the promoter targets the transgene expression to photoreceptors. In another variation, the promoter restricts expression to photoreceptors only. In another variation, the promoter is the rhodopsin kinase (RK) promoter.

A sequence to be expressed in a photoreceptor. In a variation the invention provides an expression construct comprising a sequence to be expressed in a photoreceptor-specific manner. In a further variation, the sequence to be expressed comprises a gene encoding Kv8.2. In a further variation, the sequence to be expressed comprises SEQ ID NO. 2.

The foregoing and other features and advantages of this disclosure will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 7 provides the Stage III proof of concept studies.

FIG. 11 is a table demonstrating protocol for mice pilot studies.

FIG. 20 and FIG. 21, taken together, illustrate a sequence alignment of the human KCNV2 (SEQ ID NO: 1) and the codon-optimized variant thereof SEQ ID NO: 2.

SEQUENCE LISTING

Figure 1:
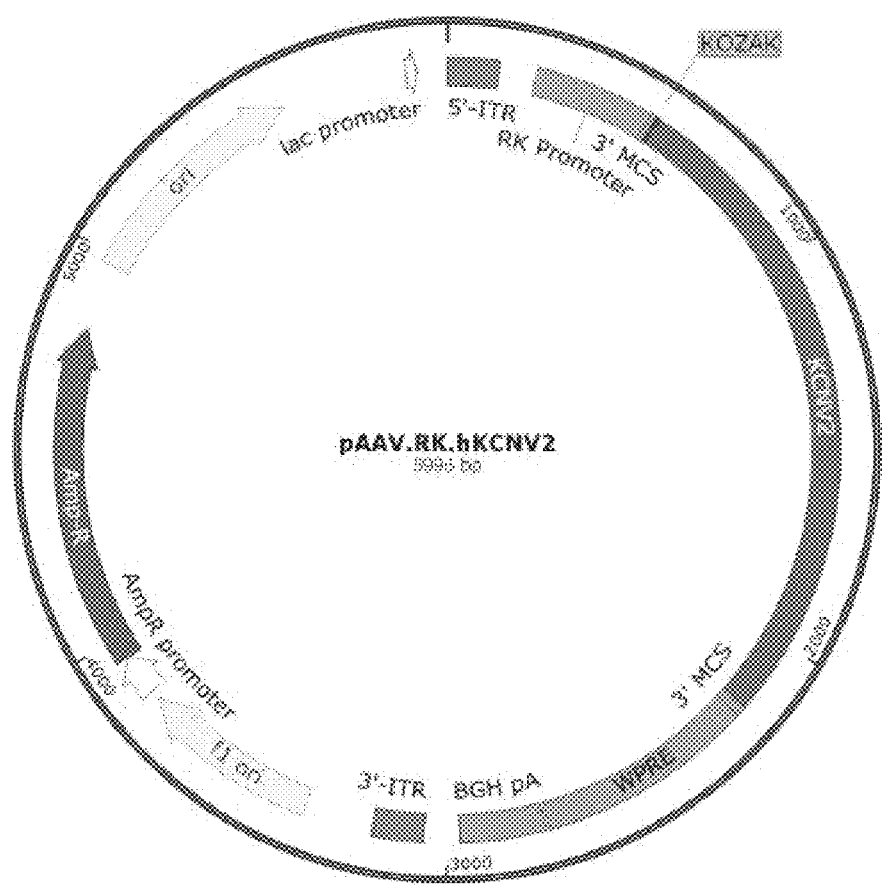
FIG. 1 illustrates a schematic map of a first construct.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~40 kb), which was created on May 18, 2022 which is incorporated by reference herein.

DETAILED DESCRIPTION

We disclose novel recombinant nucleic acid molecules, proteins, vectors, and related methods of use to treat cone dystrophy with supernormal rod response [CDSRR] (Retinal cone dystrophy 3B, OMIM 610356) and related pathologies indicated by KCNV2 gene. CDSRR is a rare, recessive, and inherited retinopathy that is characterized by poor visual acuity (due to central scotoma), photophobia, severe color vision deficits, and occasionally, nystagmus and strabismus are also present. In some patients, the fundus appears normal but foveal or parafoveal atrophy, a macular bull's eye, hyperfluorescence anomalies, and a generalized fine pigmentary retinopathy have been reported. There may be some temporal pallor in the optic nerves.

Clinical symptoms may be restricted to visual loss with no other tissues or organs affected. Most government agencies define legal blindness as a corrected visual acuity (central vision) of 20/200 or worse in the best seeing eye. This means that what the legally blind person can see at 20 feet, the average person can see clearly at 200 feet. In CDSRR studies have shown that visual acuity can vary from person to person but is around 20/160 on average but can eventually progress to legally blind levels. No specific treatment is available to either reduce or prevent the progression of visual loss, leaving patients with a poor prognosis and declining quality of life as they age. As prognosis relates to the likelihood of healing, treating, or curing a condition, the poor prognosis for CDSRR and other KCNV2-associated pathologies means there is little chance for recovery as there is no cure or treatment currently available. Low vision aids and tinted lenses are the only resources available to patients to try to ameliorate the vision loss symptoms. Several studies have indicated the progressive nature of central vision loss in CDSRR patients, but large-scale natural history studies have not yet been completed to assess the full extent of disease progression.

The rarity of this disease (the estimated number of affected individuals worldwide is 1 in 1,000,000) qualifies it for rare disease definition, preventing it from being addressed by the pharmaceutical industry because it provides little financial incentive for the private sector to make and market new medications to treat or prevent it. However, the availability of electroretinography (ERG) and genetic testing allows for accurate and early CDSRR diagnosis and supports the development of a treatment for this disorder. The recessive mode of inheritance for CDSRR and slow-progressive nature makes it a good candidate for a one off viral-based gene therapy (gene supplementation) treatment.

Among the causative agents of CDSRR is a mutation in the potassium channel, voltage-gated, subfamily V, member 2 gene (KCNV2). In some CDSRR patients, mutations in the KCNV2 gene that encodes the Kv8.2 voltage-gated potassium ($K^+$) channel subunit are present. More than 95 different CDSRR-causing variants in KCNV2 have now been identified worldwide and include missense, nonsense, intragenic deletions, out-of-frame insertions amongst other variants. The different variants have shown to affect Kv8.2 differently, with some mutations generating non-conducting channels, whereas other mutations prevented channel formation altogether. This suggests the existence of distinct mechanisms involved in the disease pathology but also that all variants generate a non-functional protein, making CDSRR a good candidate for gene replacement therapy Kv8.2 is a member of a group of "modifier/silent" channel proteins that do not form channels by themselves but require a cognate partner; for Kv8.2, this is Kv2.1 (encoded by KCNB1), a member of the Shab family of subunits that generate delayed rectifier currents that regulate the rate of repolarization of action potentials. In the eye, both the Kv8.2 and Kv2.1 subunits are located exclusively on the cytoplasmic membrane of the inner segments of cone and rod photoreceptor cells, the cells responsible for initiating the light transduction cascade of the visual response. However, missense mutations in KCNV2 have also been shown to cause epilepsy in humans, indicating it might also be expressed in the brain. The electroretinogram (ERG) disease phenotype indicates that mutations in KCNV2 results in a loss of function of the Kv8.2 subunit leading to the functional abolition of the Kv2.1/Kv8.2 heteromer. Ultimately, this then alters the sensitivity of the retina to light and thereby the fundamental physiological processes whereby the dynamic range of vision is modulated under different levels of illumination.

Evidence suggests that mutations in KCNV2 affect both cone and rod photoreceptors, which is reflected in abnormal ERG recordings for both photoreceptors and widespread throughout the retina, however, in some patients the morphological changes observed appear to be more pronounced in cones. High resolution imaging of the retina using spectral domain optical coherence tomography (SD-OCT) in CDSRR patients has revealed that gross morphological abnormalities usually in the central retina. These include inner/outer segment (IS/OS) junction, profound foveal depth reduction, cone photoreceptor mosaic disruption with patches of absent cones and overall reduced cone density. However, the mechanisms of photoreceptor cell loss within CDSRR retinas are still unknown. Moreover, how the disease differentially affects cones and rods is not clear. A recent study of abnormalities in CDSRR patients as measured by pupillometry indicate that inner-retinal function may be preserved. In a variation, therapies designed to restore outer-retinal function may be successful.

Disclosed herein are nucleic acids, transcriptional control units (TCUs), optimized gene sequences, expression constructs, and vectors for expressing genes in retinal cells, including but not limited to, cone photoreceptors and/or rod photoreceptors.

Disclosed herein are modified KCNV2 genes containing nucleic acid replacements in an unmodified KCNV2 gene (SEQ ID NO: 12), wherein the nucleic acid replacement can be one or more of those demonstrated by alignment of the human KCNV2 gene with the codon-optimized version represented by SEQ ID NO 2.

Also provided are nucleic acids, transcriptional control units (TCUs), optimized gene sequences, expression constructs, and vectors for expressing genes in photoreceptors, e.g, cone photoreceptors and/or rod photoreceptors.

Also provided are vectors, such as an adeno-associated virus (AAV) vector, containing the nucleic acid molecules, as well as isolated Kv8.2 proteins encoded by the nucleic acid molecules.

Also provided are expression constructs, comprising a variant human KCNV2 gene (SEQ ID NO: 2) under control of TCUs. In a variation, the KCNV2 is under the control of a promoter optimized for expressing genes in photoreceptors, e.g., cone photoreceptors or rod photoreceptors. In a variation, the variant human KCNV2 gene may be under the control of the rhodopsin kinase (RK) promoter (SEQ ID NO: 6).

Also provided are variants of the KCNV2 gene, e.g. SEQ ID NO: 2, with increased gene expression relative to the corresponding native human KCNV2 gene (SEQ ID NO: 12). The variants of the KCNV2 gene have improved therapeutic properties, including improved expression including an up to an average of an approximately 8-fold gene expression increase compared to wild-type, a higher difference and significant decrease in the ERG positive b-wave data compared to untreated eyes, and a higher difference and significant decrease in the ERG positive b-wave data compared to that obtained by other products. The improved properties of the disclosed KCNV2 variants (e.g., SEQ ID NO: 2) include but are not limited to increased expression as compared to the corresponding native human KCNV2 gene (SEQ ID NO: 12), increased expression as compared to the corresponding wild type KCNV2 gene (SEQ ID NO: 12), and/or improved pharmacokinetic properties compared to the corresponding native human KCNV2 gene (SEQ ID NO: 12). The improved properties may include improved transcript stability and minimized aberrant transcript splicing.

Also disclosed are methods of using one or more of the nucleic acids, transcriptional control unit (TCUs), optimized gene sequences, expression constructs, and vectors for the treatment and/or prevention of retinal disorders or dystrophies, including but not limited to CDSRR.

Also disclosed is a AAV-mediated gene augmentation therapy for KCNV2 associated Cone dystrophy with supernormal rod response.

Accordingly, in one variation we provide:

A promoter capable of directing expression of the KCNV2 gene. In a variation, the promoter targets the transgene expression to photoreceptors. In another variation, the promoter restricts expression to photoreceptors only. In another variation, the promoter is the rhodopsin kinase (RK) promoter (SEQ ID NO: 6).

A sequence to be expressed in a photoreceptor. In a variation the invention provides an expression construct comprising a sequence to be expressed in a photoreceptor-specific manner. In a further variation, the sequence to be expressed comprises a gene encoding Kv8.2. In a further variation, the sequence to be expressed comprises SEQ ID NO. 2.

The foregoing and other features and advantages of this disclosure will become more apparent from the following detailed description of several embodiments which proceeds with reference to the accompanying figures.

Terms

Unless otherwise noted, technical terms are used according to conventional usage. Definitions of common terms in molecular biology may be found in Krebs et al. (eds.), Lewin's genes XII, published by Jones & Bartlett Learning, 2017; Kendrew et al. (eds.), *The Encyclopedia of Molecular Biology*, published by Blackwell Science Ltd., 2009 (ISBN 9780632021826). The singular terms "a," "an," and "the" include plural referents unless context clearly indicates otherwise. "Comprising A or B" means including A, or B, or A and B. Although methods and materials similar or equivalent to those described herein can be used in the practice or testing of the present disclosure, suitable methods and materials are described below. In addition, the materials, methods, and examples are illustrative only and not intended to be limiting. In case of conflict, the present specification, including explanations of terms, will control. In order to facilitate review of the various embodiments of the disclosure, the following explanations of specific terms are provided:

5' and/or 3': Nucleic acid molecules (such as, DNA and RNA) are said to have "5' ends" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a linear polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of a linked gene, are generally located 5' or upstream of the coding region. However, enhancer elements can exert their effect even when located 3' of the promoter element and the coding region. Transcription termination and polyadenylation signals are located 3' or downstream of the coding region.

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

KCNV2: The human KCNV2 gene (NCBI Reference Sequence: NM_133497.4; Ensembl gene ENSG00000168263.9 and transcript KCNV2-201 ENST00000382082.4)(SEQ ID NO: 1) was the selected transgene. The KCNV2 transcript has only one splice variant and is composed of 2 exons. The whole transcript length is 2178 base pairs long, and the coding sequence (CDS) used as the base for our studies is 1638 base pairs long.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Control: A reference standard. In some embodiments, the control is a negative control sample obtained from a healthy patient. In other embodiments, the control is a positive control sample obtained from a patient diagnosed with CDSRR. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Expression: Transcription or translation of a nucleic acid sequence. For example, an encoding nucleic acid sequence (such as a gene) can be expressed when its DNA is transcribed into RNA or an RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcriptional terminators, a start codon (ATG) in front of a protein-encoding gene, splice signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Gene: A nucleic acid sequence, typically a DNA sequence, that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

As is well known in the art, most eukaryotic genes contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed not to contribute to a mature mRNA transcript, but rather to be "spliced out" during processing of the transcript.

Gene therapy: The introduction of a heterologous nucleic acid molecule into one or more recipient cells, wherein expression of the heterologous nucleic acid in the recipient cell affects the cell's function and results in a therapeutic effect in a subject. For example, the heterologous nucleic acid molecule may encode a protein, which affects a function of the recipient cell.

Hybridization: Hybridization assays for the characterization of nucleic acids with a certain level of identity to the nucleic acid sequences as provided herein are well known in the art; see e.g. Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989). The term "hybridization" or "hybridizes" as used herein may relate to hybridizations under stringent or nonstringent conditions. Said hybridization conditions may be established according to conventional protocols described, e.g., in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of hybridizing sequences will usually require stringent hybridization and washing conditions such as, for example, conditions which range from that of 0.1×SSC, 0.1% SDS at 65° C. or 2×SSC, 60° C., 0.1% SDS to, for example, 6×SSC, 1% SDS at 65° C. As is well known, the length of the probe and the composition of the nucleic acid to be determined constitute further parameters of the hybridization conditions.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy*, 22$^{nd}$ ed., London, UK: Pharmaceutical Press, 2013, describes compositions and formulations suitable for pharmaceutical delivery of the disclosed vectors.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as vector compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a scaled vial that contains sterile contents or a syringe for injection into a subject, or lyophilized for subsequent solubilization and administration or in a solid or controlled release dosage.

Purified: The term purified does not require absolute purity; rather, it is intended as a relative term. Thus, for example, a purified protein preparation is one in which the protein (such as a KCNV2 protein) is more enriched than the peptide or protein is in its natural environment within a cell. In one embodiment, a preparation is purified such that the protein represents at least 50% of the total protein content of the preparation.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Preventing, treating or ameliorating a disease: "Preventing" a disease (such as retinal disorders) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A tissue-specific promoter is a promoter that directs/initiated transcription primarily in a single type of tissue or cell. For example, a photoreceptor-specific promoter is a promoter that directs/initiates transcription in photoreceptor cells to a substantially greater extent than other cell types.

Protein: A biological molecule expressed by a gene or other encoding nucleic acid (e.g., a cDNA) and comprised of amino acids.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule. As used herein, "recombinant AAV" refers to an AAV particle in which a recombinant nucleic acid molecule (such as a recombinant nucleic acid molecule encoding a Kv8.2) has been packaged.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Retina: The retina is composed of the retinal pigment epithelium (RPE) cell layer and three layers of neurosensory cells; namely (from outer to inner), the outer nuclear layer (containing rod and 15 cone photoreceptor cells), the inner nuclear layer (containing bipolar cells), and the ganglion cell layer. Retinal disorders or dystrophies can be defined as diseases of the retina, characterized by progressive loss of photoreceptor cells and concomitant loss of vision. The retinal disorders or dystrophies may be inherited retinal disorders or dystrophies.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals.

Therapeutically effective amount: The amount of agent, such as a disclosed recombinant AAV vector encoding KCNV2, that is sufficient to prevent, treat (including prophylaxis), reduce and/or ameliorate the symptoms and/or underlying causes of a disorder or disease, for example to prevent, inhibit, and/or treat retinal disorders. For example, this can be the amount of a recombinant AAV vector encoding a novel KCNV2 gene as described herein that produces sufficient amounts of KCNV2 to restore photoreceptor function.

In one example, a desired response is to restore photoreceptor function in a subject (such as a subject with CDSRR), for example as measured by electroretinogram (ERG) recordings. The ERG recordings (A-wave, b-wave, c-wave) do not need to be completely restored to that of normal healthy subjects without CDSRR for the method to be effective. For example, administration of a therapeutically effective amount of a vector (such as a KCNV2 encoding vector) as disclosed herein can increase the photopic or scotopic ERG b-wave by a desired amount, for example by at least 10%, at least 20%, at least 30%, at least 40%, at least 50%, at least 60%, at least 70%, at least 80%, at least 90%, at least 95%, at least 98%, at least 100% or more, as compared to a suitable control.

It is understood that to obtain a therapeutic response to the disease or condition can require multiple administrations of a therapeutic agent. Thus, a therapeutically effective amount encompasses a fractional dose that contributes in combination with previous or subsequent administrations to attaining a therapeutic outcome in the patient. For example, a therapeutically effective amount of an agent can be administered in a single dose, or in several doses, for example daily, during a course of treatment. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an adeno-associated virus (AAV) vector. In some embodiments, the vector is a gamma-retroviral vector, a lentiviral vector, or an adenoviral vector.

Novel KCNV2 Gene

A nucleic acid molecule is provided that encodes a protein with Kv8.2 activity comprising nucleotide sequence set forth as SEQ ID NO. 2, or a nucleic acid sequence at least 95%, at least 96%, at least 97%, at least 98%, or at least 99% identical thereto.

A nucleic acid molecule is provided that hybridizes under stringent conditions to the complementary strand of the nucleotide sequence set forth as SEQ ID NO. 2, or a nucleic acid sequence at least 95%, at least 96%, at least 97%, at least 98%, or at least 99% identical thereto.

A nucleic acid molecule is provided that is degenerate as a result of the genetic code to the nucleotide sequence set forth as SEQ ID NO. 2, or a nucleic acid sequence at least 95%, at least 96%, at least 97%, at least 98%, or at least 99% identical thereto.

As discussed in Example 1, the nucleotide sequence encoding Kv8.2 was codon-optimized for improved expression. An exemplary optimized KCNV2 sequence is provided as SEQ ID NO: 2.

Disclosed herein are variants of the KCNV2 gene with increased expression relative to the corresponding native human KCNV2. SEQ ID NO: 2 has improved therapeutic properties, including improved photoreceptor therapeutic properties, compared to an unmodified KCNV2 gene, including a human wild type KCNV2 gene disclosed as SEQ ID NO: 1, the coding region disclosed at SEQ ID NO: 12. The improved properties of the disclosed KCNV2 variants include but are not limited to increased protein synthesis, a more stable mRNA, increase the rate of translation elongation, and/or improved pharmacokinetic properties. The improved properties may include stable transgene and protein expression, enhanced recovery, and improved visual function.

A variant of a KCNV2 polynucleotide may be defined as any variant of SEQ ID NO: 2, including naturally occurring variants in the nucleic acid sequence. The variant may be defined as having at least about 60%, 70%, 80%, 90%, 95%, 96%, 97%, 98%, or 99% sequence identity to SEQ ID NO: 2, wherein the polypetide translated from the variant sequence retains its functionality. The variant may be defined as having at least about 60%, 70%, 80%, 90%, 95%, 96%, 97%, 98%, or 99% sequence identity to SEQ ID NO: 2, wherein the polypetide translated from the variant sequence, SEQ ID NO: 11, has the ability to rescue photoreceptor function. In certain variations, the variant is a codon optimized version of the coding sequence.

The expression constructs contemplated by the disclosure may recue cone photoreceptor function. Rescuing cone photoreceptor function can be defined as restoring at least about 10%, 20%, 30%, 40%, 50%, 60%, 70%, 80% 90%, 95%, 96%, 97%, 98%, 99% or 100% of cone photoreceptor function. Cone photoreceptor function can be analyzed by any suitable standard technique known to the person skilled in the art, for example, by electroretinogram (ERG) analysis of retinal responses. Rod photoreceptor function can be analyzed by any suitable standard technique known to the person skilled in the art, for example, by ERG analysis of retinal responses.

Rescuing photoreceptor function can also be defined as prolonging photoreceptor survival. Prolonging photoreceptor survival can be defined as extending the time that a photoreceptor (e.g., a cone photoreceptor and/or a rod photoreceptor) is functional or present by about 10%, 20%, 30%, 40%, 50%, 60%, 70%, 80%, 90%, 95%, 96%, 97%, 98%, 99%, 100% or more than 100% when compared with a photoreceptor affected by a dystrophy. Examples of prolonging photoreceptor survival also include improving ERG activity or slowing loss of ERG activity, improving retinal sensitivity or slowing/halting progressive loss of retinal sensitivity, slowing or halting loss of photoreceptor cells, slowing or halting thinning of the outer retinal layer, improving vision or slowing/halting vision loss.

The expression construct may comprise one or more transcription control units operably linked to a KCNV2 gene. In a variation, the KCNV2 gene is SEQ ID NO: 2. In some variations, the KCNV2 gene is codon optimized.

Thus, nucleic acid molecules (for example, cDNA or RNA molecules) encoding Kv8.2, as well as purified forms of the Kv8.2, are provided. In several embodiments, the nucleic acid molecules can be expressed in a host cell (such as a mammalian cell) to produce Kv8.2.

The genetic code can be used to construct a variety of functionally equivalent nucleic acid sequences, such as nucleic acids which differ in sequence but which encode the same polypeptide sequence.

Nucleic acid molecules disclosed herein can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Nucleic acids can also be prepared by amplification methods. Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as bacteria, plant, yeast, insect and mammalian cells. DNA sequences disclosed herein can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells such as the COS, CHO, HeLa and myeloma cell lines, can be used to express the disclosed novel nucleotide sequences. Methods of stable transfer, meaning that the foreign DNA is continuously maintained in the host, are known in the art.

The expression of disclosed nucleic acids can be achieved by operably linking the DNA or cDNA to a promoter (which is either constitutive or inducible), followed by incorporation into an expression cassette. The promoter can be any promoter of interest, including a photoreceptor-specific promoter, such as the rhodopsin kinase (RK) promoter (SEQ ID NO: 6). Other exemplary promoters include but are not limited to, CAG (hybrid CMV early enhancer/chicken b-actin promoter), CBA (chicken b-actin promoter), CBh (hybrid form of the CBA promoter), CMV (human cytomegalovirus promoter), CB (regulatory element composed of the cytomegalovirus (CMV) immediate early enhancer, chicken b-actin promoter with first intron/exon junction, hybrid chicken b-actin and rabbit b-globulin intron/exon junction), CBSB (containing a shorter CMV immediate enhancer sequence than CB promoter), GRK1 (human G protein-coupled receptor kinase 1 promoter), pRLBP1 (shortened human retinaldehyde binding protein 1 (RLBP1) promoter, hCAR (human cone arrestin promoter, PR1.7 and PR2.1 (versions of human L-opsin promoter), IRBP (human interphotoreceptor retinoid-binding protein enhancer), RS/IRBP (combination of the human retinoschisin proximal promoter and the human interphotoreceptor retinoid-binding protein enhancer), pRHO (rhodopsin promoter), and hPDE6b (short human phosphodiesterase 6b promoter).

Optionally, a regulatory element, such as any one or more of KOZAK consensus sequence (SEQ ID NO: 8), a Woodchuck Hepatitis Virus (WHP) Posttranscriptional Regulatory Element (WPRE)(SEQ ID NO: 9); and/or a bovine growth hormone polyadenylation (BGH poly(A))(SEQ ID NO: 10), is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For E. coli, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for E. coli and calcium phosphate treatment, electroporation or lipofection for mammalian cells. Cells transformed by the cassettes can be selected by resistance to antibiotics conferred by genes contained in the cassettes, such as the amp, GPt, neo, and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the disclosed Kv8.2 can be purified according to standard procedures in the art, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The disclosed polypeptides need not be 100% pure. Once purified, partially or to homogeneity as desired, if to be used therapeutically, the polypeptides should be substantially free of endotoxin.

Recombinant Vectors and Gene Therapy Applications

In current practice, gene therapy implies functional replacement of a dysfunctional gene in which no functional protein is produced, with a wild-type copy that restores function. Gene therapy is a promising approach in the treatment of inherited and common complex disorders of the retina and preclinical and clinical studies have validated the use of adeno-associated viral vectors (AAV) as a safe and efficient gene delivery vehicle. AAV-mediated gene replacement therapy has been achieved in different tissues and systems including liver, muscle, blood cells and retina.

Several animal models of inherited photoreceptor degeneration have undergone successful treatment by gene supplementation therapy, and to date visual rescue has been achieved on morphological, functional, and behavioral levels. There are 43 ongoing or completed clinical trials that are using or have used AAV delivery systems as a means of correcting genetic faults for different types of inherited retinal disorder (clinicaltrials.gov, search completed on Nov. 16, 2020). Another five clinical trials (three ongoing and two completed) are also using or have used AAV to deliver therapeutics for age-related macular degeneration.

AAV vectors have been demonstrated to be an acceptable delivery method for photoreceptor cell targeting both in efficiency and specificity. AAV vectors have been shown to have high affinity for photoreceptor cells while also offering a non-toxic, non-pathogenic and low immunogenic profile. This has demonstrated successful application of gene therapy to retinal disorder and vision loss models. Among the different AAV serotypes currently available the most commonly used ones for targeting retinal cells have been AAV2/2, AAV2/8, AAV2/9, AAV2/5, AAV2/7m8, AAV2/Anc80_L065 serotypes.

Any of the above discussed recombinant nucleic acid molecules can be included in a vector (such as a AAV vector) for expression in a cell or a subject.

The nucleic acid sequences disclosed herein are useful in production of vectors (such as rAAV vectors), and are also useful in antisense delivery vectors, gene therapy vectors, or vaccine vectors. In certain embodiments, the disclosure provides for gene delivery vectors, and host cells which contain the nucleic acid sequences disclosed herein. In some embodiments, the selected vector may be delivered to a subject by any suitable method, including intravenous injection, ex-vivo transduction, transfection, electroporation, liposome delivery, membrane fusion techniques, high velocity DNA-coated pellets, viral infection, or protoplast fusion, to introduce a transgene into the subject.

In certain embodiments, the disclosure relates to virus particle, e.g., capsids, containing the KCNV2 nucleic acid sequences SED ID NO: 2 disclosed herein. The virus particles, capsids, and recombinant vectors are useful in delivery of the nucleic acid sequences to a target cell. The nucleic acids may be readily utilized in a variety of vector systems, capsids, and host cells. In certain embodiments, the nucleic acids are in vectors contained within a capsid comprising cap proteins, including AAV capsid proteins vp1, vp2, vp3 and hypervariable regions.

In certain embodiments, the KCNV2 nucleic acid sequences may be a part of any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon.

In certain embodiments, a vector may be a lentivirus based (containing lentiviral genes or sequences) vector, e.g., having nucleic acid sequences derived from VSVG or GP64 pseudotypes or both. In certain embodiments, the nucleic acid sequences derived from VSVG or GP64 pseudotypes may be at least one or two or more genes or gene fragments of more than 1000, 500, 400, 300, 200, 100, 50, or 25 continuous nucleotides or nucleotides sequences with greater than 50, 60, 70, 80, 90, 95 or 99% identity to the gene or fragment.

In some embodiments, the nucleic acid and promotor sequences disclosed herein are useful in production of AAV vectors. AAV belongs to the family Parvoviridae and the genus Dependovirus. AAV is a small, non-enveloped virus that packages a linear, single-stranded DNA genome. Both sense and antisense strands of AAV DNA are packaged into AAV capsids with equal frequency. The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008).

AAV vectors typically contain a transgene expression cassette between the ITRs that replaces the rep and cap genes. Vector particles are produced by the co-transfection of cells with a plasmid containing the vector genome and a packaging/helper construct that expresses the rep and cap proteins in trans. During infection, AAV vector genomes enter the cell nucleus and can persist in multiple molecular states. One common outcome is the conversion of the AAV genome to a double-stranded circular episome by second-strand synthesis or complementary strand pairing.

In the context of AAV vectors, the disclosed vectors typically have a recombinant genome comprising the following structure:

(5'AAV ITR)-(promoter)-(transgene)-(3'AAV ITR)

As discussed above, these recombinant AAV vectors contain a transgene expression cassette between the ITRs that replaces the rep and cap genes. Vector particles are produced, for example, by the co-transfection of cells with a plasmid containing the recombinant vector genome and a packaging/helper construct that expresses the rep and cap proteins in trans.

The transgene can be flanked by regulatory sequences such as a 5' Kozak sequence and/or a 3' polyadenylation signal.

The AAV ITRs, and other selected AAV components described herein, may be readily selected from among any AAV serotype, including, without limitation, AAV1, AAV2, AAV2-QuadyF, AAV2.7m8, AAV3, AAV4, AAV5, AAV6, AAV7, AAV8, AAV8(Y733F), AAV9, Anc80, AAV7m8, AAVrh10, AAV-PHP.cB, AAV-PHP.S, AAV-DJ, AAV-DJ/8, AAV2.GL, AAV2.NN, AAVAnc80_L065 and function variants of any thereof. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like. It will be understood that the disclosure encompasses use of an AAV genome of other serotypes that may not yet have been identified or characterized.

In some embodiments, the recombinant AAV vector genome can have a photoreceptor-specific promoter, such as rhodopsin kinase (RK) or any modifications thereof. The recombinant AAV vector genome can have any promoter known in the art including those disclosed herein and/or those disclosed in Kaneshiro, K., Wu, Z., Li, T., Sieving, P., & Colosi, P. (2011). Evaluation of Viral and Human Retinal Promoters in AAV8 Vectors. *Investigative Ophthalmology & Visual Science*, 52(14), 491.

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin Microbiol Rev* 21(4):583-593, 2008).

Methods for producing rAAV suitable for gene therapy are known (see, for example, U.S. Patent Application Nos. 2012/0100606; 2012/0135515; 2011/0229971; and 2013/0072548; and Ghosh et al., *Gene Ther* 13(4):321-329, 2006), and can be utilized with the recombinant nucleic acid molecules and methods disclosed herein.

In some embodiments, the nucleic acids disclosed herein are part of an expression cassette or transgene. See e.g., US Pat. App. Pub. 20150139953. The expression cassette is composed of a transgene and regulatory sequences, e.g., promotor and 5' and 3' AAV inverted terminal repeats (ITRs). In one desirable embodiment, the ITRs of AAV serotype 2 or 8 are used. However, ITRs from other suitable serotypes may be selected. An expression cassette is typically packaged into a capsid protein and delivered to a selected host cell.

In some embodiments, the disclosure provides for a method of generating a recombinant adeno-associated virus (AAV) having an AAV serotype capsid, or a portion thereof. Such a method involves culturing a host cell which contains a nucleic acid sequence encoding an adeno-associated virus (AAV) serotype capsid protein; a functional rep gene; an expression cassette composed of AAV inverted terminal repeats (ITRs) and a transgene; and sufficient helper functions to permit packaging of the expression cassette into the AAV capsid protein. See e.g., US Pat. App. Pub. 20150139953.

In some embodiments, the disclosure relates to recombinant vectors comprising a photoreceptor specific promotor nucleic acid sequence in operable combination with transgene. The transgene is a nucleic acid sequence, heterologous to the vector sequences flanking the transgene, which encodes Kv8.2 as disclosed herein, and optionally one or more additional proteins of interest. The nucleic acid coding sequence is operatively linked to regulatory components in a manner which permits transgene transcription, translation, and/or expression in a host cell.

The expression cassette can be carried on any suitable vector, e.g., a plasmid, which is delivered to a host cell. The plasmids useful in this disclosure may be engineered such that they are suitable for replication and, optionally, integration in prokaryotic cells, mammalian cells, or both. These plasmids (or other vectors carrying the 5' AAV ITR-heterologous molecule-3' ITR) contain sequences permitting replication of the expression cassette in eukaryotes and/or prokaryotes and selection markers for these systems. Preferably, the molecule carrying the expression cassette is transfected into the cell, where it may exist transiently. Alternatively, the expression cassette (carrying the 5' AAV ITR-heterologous molecule-3' ITR) may be stably integrated into the genome of the host cell, either chromosomally or as an episome. In certain embodiments, the expression cassette may be present in multiple copies, optionally in head-to-head, head-to-tail, or tail-to-tail concatamers. Suitable transfection techniques are known and may readily be utilized to deliver the expression cassette to the host cell.

Generally, when delivering the vector comprising the expression cassette by transfection, the vector and the relative amounts of vector DNA to host cells may be adjusted, taking into consideration such factors as the selected vector, the delivery method and the host cells selected. In addition to the expression cassette, the host cell contains the sequences which drive expression of the AAV capsid protein in the host cell and rep sequences of the same serotype as the serotype of the AAV ITRs found in the expression cassette, or a cross-complementing serotype. Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell.

Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

The AAV techniques can be adapted for use in these and other viral vector systems for in vitro, ex vivo or in vivo gene delivery. The in certain embodiments the disclosure contemplates the use of nucleic acids and vectors disclosed herein in a variety of rAAV and non-rAAV vector systems. Such vectors systems may include, e.g., lentiviruses, retroviruses, poxviruses, vaccinia viruses, and adenoviral systems, among others.

In some embodiments, it is contemplated that viral particles, nucleic acids and vectors disclosed herein are useful for a variety of purposes, including for delivery of therapeutic molecules for gene expression of therapeutic proteins.

Therapeutic proteins encoded by the nucleic acids (e.g., operably in combination with promoters) reported herein include those used for treatment of retinal disorders.

In some embodiments, a method of restoring retinal function in a subject with CDSRR is disclosed. The method comprises administering to the subject a therapeutically effective amount of a vector (such as an AAV vector, a lentiviral vector, or a retroviral vector) including KCNV2 nucleic acid sequences as described herein. In some embodiments, the subject is a subject with a retinal disorder, such as CDSRR.

In a variation, we delivery of the novel KCNV2 gene in the AAV2/8 serotype which was shown to have up to 100-fold higher transduction capacity compared to some other known capsids. In the retina, AAV2/8 has shown to be a more efficient vector compared to AAV2/2 and AAV2/5; it provided both faster onset and stronger and higher transgene expression, especially in photoreceptors.

In some embodiments, this disclosure relates to methods of gene transfer for the treatment of CDSRR using an adeno-associated viral serotype 8 (AAV2/8) vector carrying a codon-optimized human KCNV2 (Potassium Voltage-Gated Channel Modifier Subfamily V Member 2). In a further variation, this disclosure relates to methods of gene transfer for the treatment of CDSRR using an adeno-associated viral serotype 8 (AAV2/8) vector carrying a codon-optimized human KCNV2 under the expression of the rhodopsin kinase (RK) promoter. This vector may be referred to herein as AAV2/8.RK.hKCNV2.

Delivery of the vector encoding the transgene can be, for example, by direct administration to the subject, e.g., by subretinal injection of the vector. In a further example, delivery of the vector can be, for example, by injection of the vector in the macular and/or foveal region to one or both eyes of a patient at any disease state.

In a further variation, delivery of the vector encoding the transgene can be, for example, by direct administration to the subject, e.g., by subretinal injection of the vector. In a further example, delivery of the vector can be, for example, by injection of the vector in the macular and/or foveal region to one or both eyes of a patient at any disease state. In this variation, the AAV2/8.RK.hKCNV2 may be delivered in neutral phosphate buffered saline with Pluronic F68 (0.001%), 0.10 ml, dose range of 5E9 to 5E11 vector genomes.

In general, delivery may be by direct retinal, subretinal or intravitreal delivery of a nucleic acid, such as a vector, as disclosed herein, by injection. In an example, delivery may be by injection to the retinal, subretinal space or intravitreal space.

We therefore also provide a method of treating or preventing dystrophies, in particular CDSRR in a patient in need thereof, comprising administering a therapeutically effective amount of a nucleic acid, such as a vector, as disclosed herein to the patient by direct retinal, subretinal or intravitreal injection.

In a related aspect, the invention provides for use of a nucleic acid, such as a vector, as disclosed herein in a method of treating or preventing retinal disorders, such as dystrophies, in particular CDSRR, by administering said vector to a patient by direct retinal, subretinal or intravitreal injection.

Additionally, we provide the use of a nucleic acid, such as a vector, as disclosed herein in the manufacture of a medicament for treating or preventing retinal disorders, such as dystrophies, in particular CDSRR by direct retinal, subretinal or intravitreal injection.

The invention also provides a nucleic acid, such as a vector, as disclosed herein for use in the treatment of retinal disorders, dystrophies, in particular CDSRR, wherein said vector is administered directly into the retinal, subretinal space or intravitreal space.

The administration of the nucleic acid, such as a vector, as disclosed herein is typically by direct retinal or subretinal injection. This includes direct delivery to cone photoreceptor cells and/or the rod photoreceptor cells.

Optionally, the compositions of the disclosure may contain other pharmaceutically acceptable excipients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The recombinant virus particles, capsids, or vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the eye), oral, inhalation, intranasal, intratracheal, intraarterial, intraocular, intravenous, intramuscular, subcutaneous, intradermal, and other parental routes of administration. Routes of administration may be combined, if desired.

Dosages of the recombinant virus particles, capsids, or vectors will depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1 \times 10^9$ to $1 \times 10^{16}$ genomes virus vector.

Recombinant viral vectors of the disclosure provide an efficient gene transfer vehicle which can deliver a selected protein to a selected host cell in vivo or ex vivo even where the organism has neutralizing antibodies to the protein. In one embodiment, the vectors disclosed herein and the cells are mixed ex vivo; the infected cells are cultured using conventional methodologies; and the transduced cells are re-infused into the patient.

Turning to FIG. 1, a disclosed vector. A vector for delivering the disclosed codon optimized KCNV2 gene of SEQ ID NO: 2 may have one or more of the following elements:
Vector of serotype AAV2/8
Rhodopsin kinase (RK) promoter (SEQ ID NO: 6)
Codon optimized KCNV2 gene of SEQ ID NO: 2
Regulatory elements including, KOZAK consensus sequence (SEQ ID NO: 8) in between the promoter and the KCNV2 gene, a Woodchuck Hepatitis Virus (WHP) Posttranscriptional Regulatory Element (WPRE) (SED ID NO: 9) after the KCNV2 gene and a bovine growth hormone polyadenylation (BGH poly(A)) (SEQ ID NO: 10) signal downstream of the WPRE. The disclosed vector may have the nucleotide sequence of SEQ ID NO: 3.

Figure 2:
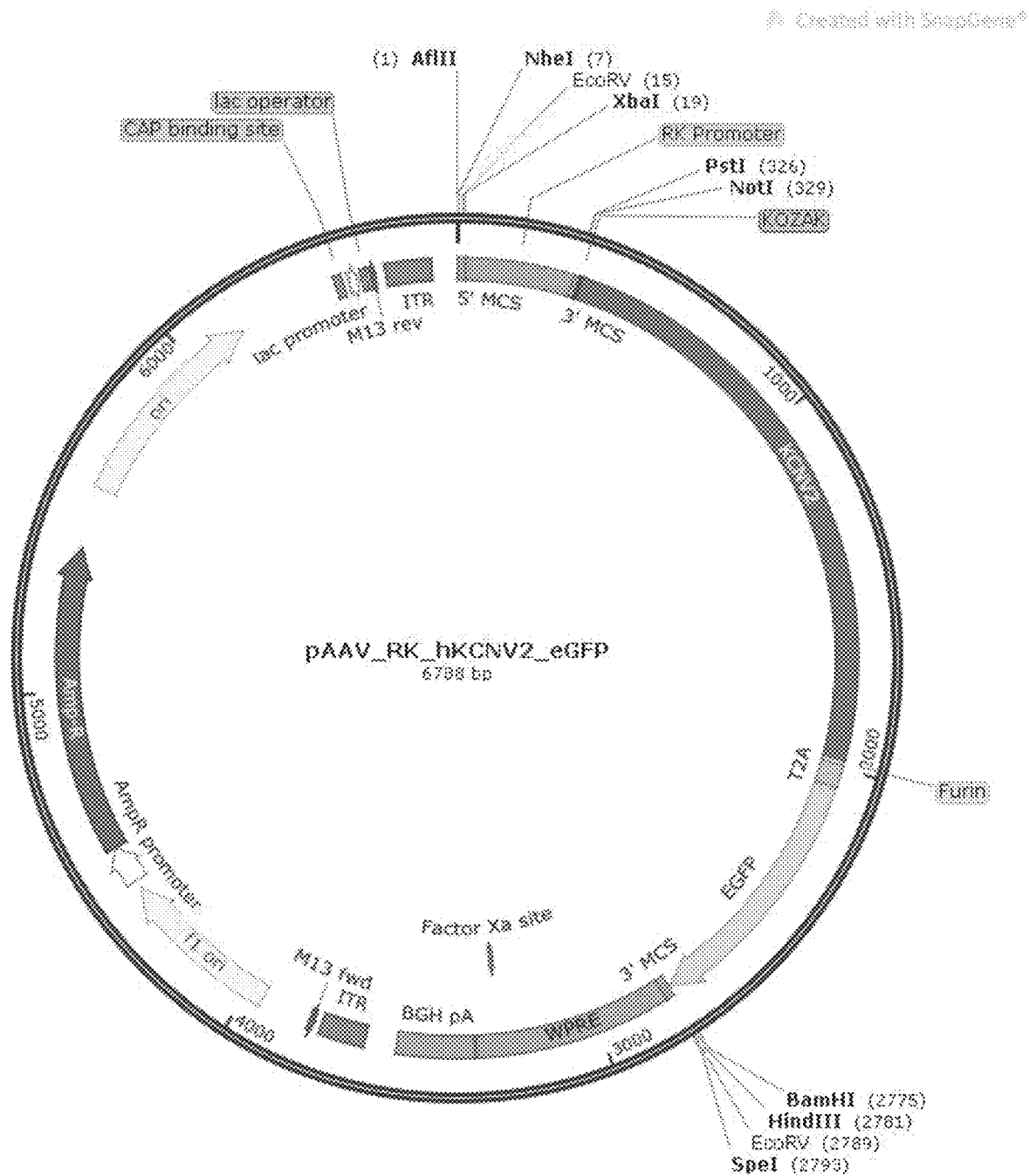
FIG. 2 illustrates a schematic map of a second construct.

Turning to FIG. 2, a second disclosed vector. A vector for delivering the disclosed codon optimized KCNV2 gene of SEQ ID NO: 2 may have one or more of the following elements:
AAV Vector
Rhodopsin kinase (RK) promoter (SEQ ID NO: 6)
Codon optimized KCNV2 gene of SEQ ID NO: 2
EGFP enhanced green fluorescent protein
Regulatory elements including, KOZAK consensus sequence (SEQ ID NO: 8) in between the promoter and the KCNV2 gene (SEQ ID NO: 2), a Woodchuck Hepatitis Virus (WHP) Posttranscriptional Regulatory Element (WPRE) (SEQ ID NO: 9) after the KCNV2 gene (SEQ ID NO:2) and a bovine growth hormone polyadenylation (BGH poly(A))(SEQ ID NO: 10) signal downstream of the WPRE (SEQ ID NO: 9).

Figure 3:
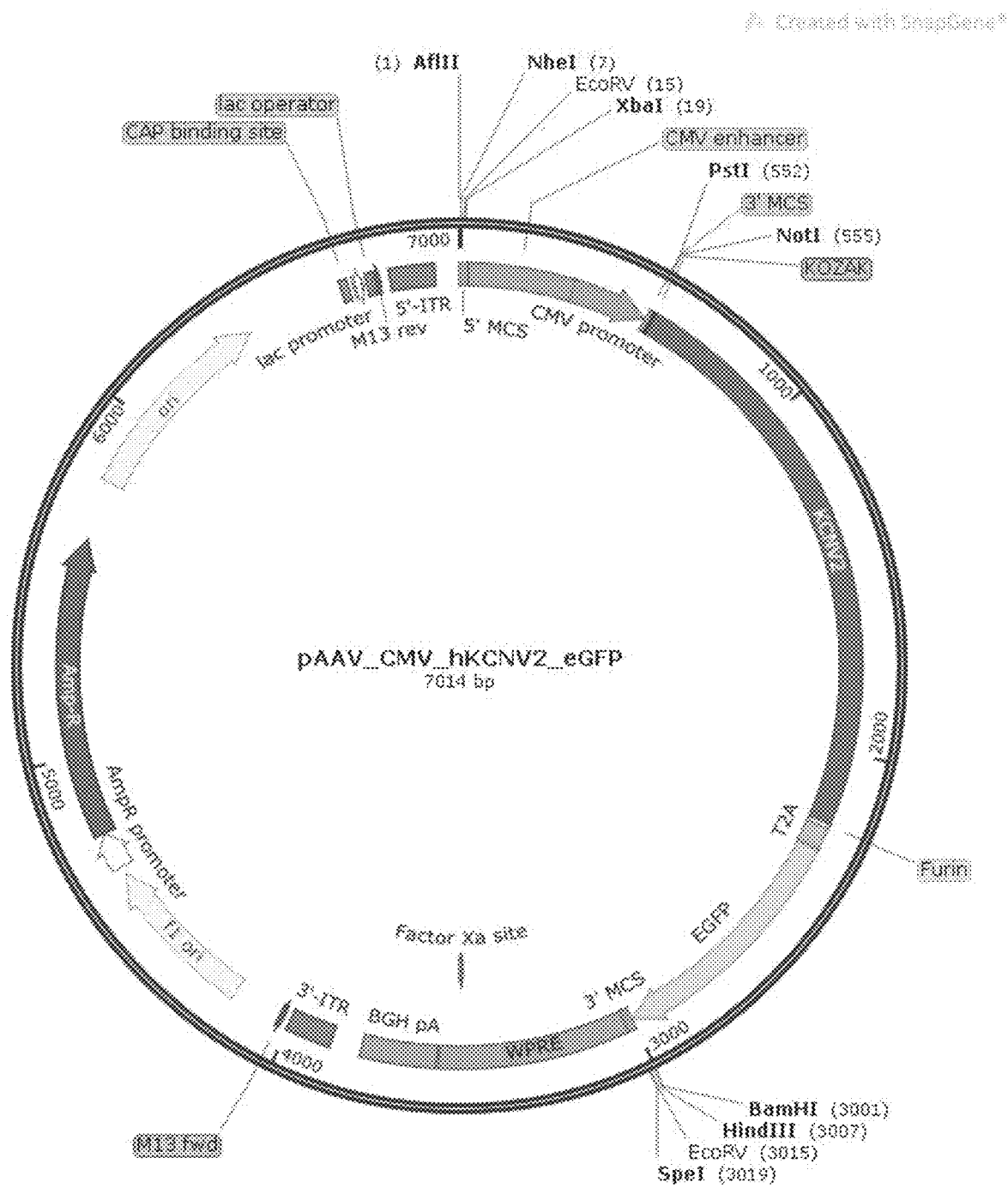
FIG. 3 illustrates a schematic map of a third construct.

Turning to FIG. 3, a third disclosed vector. A vector for delivering the disclosed codon optimized KCNV2 gene of SEQ ID NO: 2 may have one or more of the following elements:
AAV Vector
Rhodopsin kinase (RK) promoter (SEQ ID NO: 6)
Codon optimized KCNV2 gene of SEQ ID NO: 2
EGFP enhanced green fluorescent protein
Regulatory elements including, KOZAK consensus sequence (SEQ ID NO: 8) in between the promoter and the KCNV2 gene (SEQ ID NO: 2), a CMV promoter (SEQ ID NO: 7), a Woodchuck Hepatitis Virus (WHP) Posttranscriptional Regulatory Element (WPRE)(SEQ ID NO: 9) after the KCNV2 gene and a bovine growth hormone polyadenylation (BGH poly(A)) signal (SEQ ID NO: 10) downstream of the WPRE (SEQ ID NO: 9).

Figure 4:
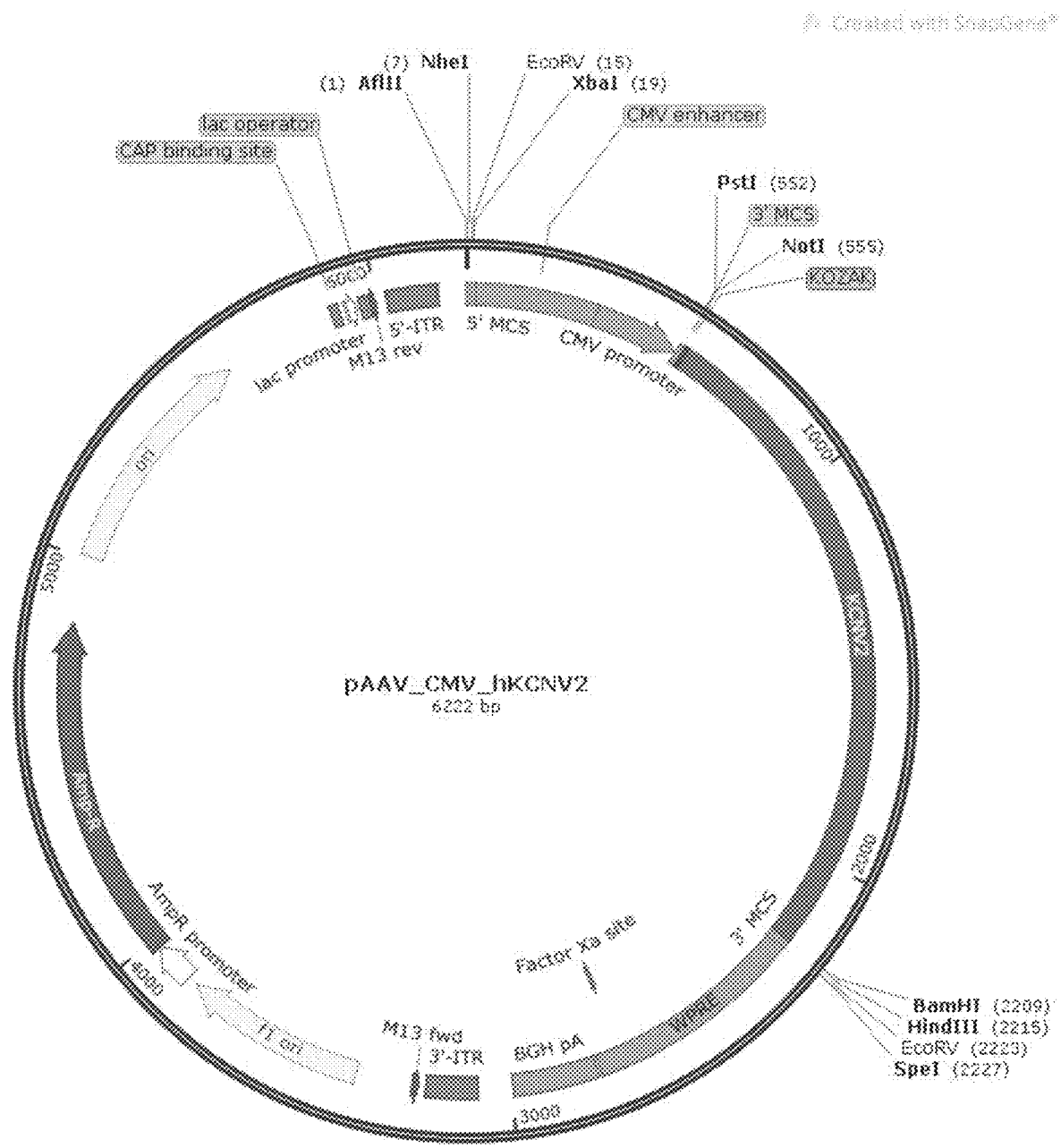
FIG. 4 illustrates a schematic map of a fourth construct.

Turning to FIG. 4, a fourth disclosed vector. A vector for delivering the disclosed codon optimized KCNV2 gene of SEQ ID NO: 2 may have one or more of the following elements:
AAV Vector
Rhodopsin kinase (RK) promoter (SEQ ID NO: 6)
Codon optimized KCNV2 gene of SEQ ID NO: 2
EGFP enhanced green fluorescent protein
Regulatory elements including, KOZAK consensus sequence (SEQ ID NO: 8) in between the promoter and the KCNV2 gene (SEQ ID NO: 2), a CMV promoter (SEQ ID NO: 7), a lac promoter, a Woodchuck Hepatitis Virus (WHP)

Posttranscriptional Regulatory Element (WPRE)(SEQ ID NO: 9) after the KCNV2 gene and a bovine growth hormone polyadenylation (BGH poly(A)) signal (SEQ ID NO: 10) downstream of the WPRE. (SEQ ID NO: 9)

AAV Serotype Selection

In our exemplary disclosure, we have selected the AAV2/8 serotype which was shown to have up to 100-fold higher transduction capacity compared to some other known capsids. We have also selected the Anc80 serotype. In the retina, AAV2/8 has shown to be a more efficient vector compared to AAV2/2 and AAV2/5; it provided both faster onset and stronger and higher transgene expression, especially in photoreceptors. However, the Anc80 serotype is also used in place of the AAV2/8.

Promoter

The necessary levels of KCNV2 gene expression needed to provide rescue of retinal function are unknown, but we it is believed that expression of KCNV2 may be restricted to both cone and rod photoreceptor cells. As the KCNV2 gene encodes for a channel protein, ubiquitous expression in different retina cells could have unintended consequences. For our therapeutic construct we decided to use the already published rhodopsin kinase (RK) promoter as it restricts the transgene expression to photoreceptors only.

KCNV2 Gene

The human KCNV2 gene (NCBI Reference Sequence: NM_133497.4; Ensemble gene ENSG00000168263.9 and transcript KCNV2-201 ENST00000382082.4) (SEQ ID NO: 1) was the selected transgene in for our construct. The KCNV2 transcript has only one splice variant and is composed of two exons. The whole transcript length is 2178 base pairs long, and the coding sequence (CDS) used as the base for our studies is 1638 base pairs long (SEQ ID NO: 12).

Prior to construct design, a codon optimized version of the human KCNV2 CDS was generated using Integrated DNA Technologies (IDT)'s codon optimization tool. The rationale for this is to link codon usage to tRNA production, to improve transcript stability and to safeguard against aberrant transcript splicing. The IDT algorithm used provides the best sequence option by screening and filtering sequences to lower complexity and minimize secondary structures.

Regulatory Elements

All our transgene constructs also contained a KOZAK consensus sequence (SEQ ID NO: 8) in between the promoter and the KCNV2 gene (SEQ ID NO: 2), a Woodchuck Hepatitis Virus (WHP) Posttranscriptional Regulatory Element (WPRE)(SEQ ID NO: 9) after the KCNV2 gene (SEQ ID NO: 2) and a bovine growth hormone polyadenylation (BGH poly(A))(SEQ ID NO: 10) signal downstream of the WPRE (SEQ ID NO: 9). The KOZAK sequence (SEQ ID NO: 8) functions for protein translation initiation in eukaryotic mRNA transcripts. The WPRE (SEQ ID NO: 9) is a DNA sequence that, when transcribed, creates a tertiary structure enhancing expression. It is used to increase expression of genes delivered by viral vectors. The BGH poly(A) (SEQ ID NO: 10) is a specialized termination sequence for protein expression in eukaryotic cells which results in the formation of the poly(A) tail at the 3' end of the mRNA. In addition, the mammalian DNA viruses which replicate in the nucleus utilize the cellular polyadenylation mechanisms. The poly(A) tail is supports the stability, transport, and translation of most mRNAs.

Preparation of Vectors

The disclosed vector may be prepared by standard means known in the art for provision of vectors for therapy. Thus, well established public domain transfection, packaging and purification methods can be used to prepare a suitable vector preparation.

The construct was developed by the following steps:

1. Construct Design

The design of the therapeutic construct was done taking into consideration, what promoter should be used to achieve the desired expression levels, if the gene should be codon optimised or not, what polyA site to use and if any other known regulatory sequences should be used.

2. Construct Assembly

DNA fragments of the final construct were synthesized by Genewiz and then cloned into a pAAV backbone plasmid.

3. Packaging into AAV

Once our construct was cloned into the pAAV backbone, it was purified and a larger plasmid amount was made using commercial kits from Qiagen. The purified plasmid was sent to be packaged into AAV. The production of the AAV followed a standard protocol. A batch of AAV2/8 was made using our therapeutic plasmid and stored in dry ice.

EXAMPLES

The following examples are provided to illustrate certain particular features and/or embodiments. These examples should not be construed to limit the disclosure to the particular features or embodiments described.

Example 1

Proof-of-Concept Studies (PC) for Selected Therapeutic—AAV8.RK.hKCNV2 Gene Therapy Reduces Supernormal b-Wave Amplitude The data from our foundation studies were used to guide our decision as to which of the three potential therapeutic products tested was going to be our selected product. Based on the gene expression data which showed an average 8-fold gene expression increase compared to wild type, and the ERG positive b-wave data that showed a higher difference and significant decrease compared to untreated eyes compared to the other products, we have selected the AAV8.RK.hKCNV2 vector as our therapeutic product for the example below. However, it should be understood that other AAV serotypes are also intended including but not limited to AAV Anc80. Below we provide the validation data.

Protocol for Mice Pilot Studies Below. See FIG. 11.

1. Viral Particles Dilution and Storage

Original stock vectors were stored at −80°C. Working stocks were diluted in sterile PBS to a $1 \times 10^{12}$ vector genomes (vg)/ml, aliquoted into 20 µl aliquots in 0.2 ml sterilized PCR tubes (SSIbo UltraFlux Flat cap PCR tubes, Cat #3220-00) and also stored at −80°C. On injection day, a diluted aliquot(s) was thawed on ice (4°C) prior to injection. A new aliquot was used per each batch of injections per day. During injections the aliquot was kept on ice. Any remaining vector suspension from the thawed aliquot was discarded from use in this study.

2. Subretinal Injection

P28-35 K8.2 KO mice of both genders were placed under general anesthesia with an intraperitoneal injection of ketamine (100 mg/kg) and xylazine (20 mg/kg). Pupils were dilated with topical 1% tropicamide (MYDRIACYL; Alcon).

Under surgical microscope, a small incision was made through the temporal sclera of the eye using the tip of a 30-gauge needle. A 35-gauge stainless steel beveled or blunt needle fitted to a NanoFil syringe was inserted through the incision and viral suspension/PBS was injected into the subretinal space using an Ultra-Micro-Pump (World Precision Instrument) (SOP #1.06.08).

Each treated animal received a 1 µl subretinal injected of rAAV2/8-hGRK1-hKCNV2 ($1\times10^{12}$ GC/mL) vector (SEQ ID NO: 3) in one eye (n=10, randomly assigned left or right eye). The other eye remained uninjected. Control animals received a subretinal injection of 1 µl of sterile 1× Phosphate Buffered Solution (PBS) in one eye (n=10, randomly assigned left or right eye) while the other eye will remain un-injected serving as internal control (n=20).

OCT validation was conducted afterwards to check location and range of injection as indicated by a bullous (bleb) retinal detachment.

3. Electroretinography (ERG)

Scotopic ERG testing was carried out on KCNV2 KO mice at specific time intervals (4, 8 and 12 wk post-injection) in order to determine whether there was an improvement in the a- and b-wave amplitudes after treatment.

Mice were dark-adapted overnight (at least 8 h) before ERG experimentation, and were handled subsequently only under dim red light. ERGs were performed as previously described [6]. Mice were anesthetized using isoflurane inhalation anesthesia, pupils were dilated with topical 1% tropicamide (MYDRIACYL; Alcon). Artificial lubricant (Hydroxypropyl methylcellulose) were applied to the cornea to avoid dehydration and facilitate contact before placing ERG electrodes on each eye. For reference, a subdermal needle electrode was placed into each cheek or along the jaw line of the mouse, and a ground electrode was placed subdermal above the base of the tail.

ERG recordings were obtained using a dark-adapted single-flash intensity series by the presentation of 1-ms flashes at the following intensities (all in cd·s $m^{-2}$): 0.1, 0.3, 1, 3, 10, and 25. The time interval between consecutive flashes and the number of times the stimulus were repeated (for subsequent averaging) and varied according to stimulus intensity; 10 s and 4 repeats for 0.1-3 cd·s $m^{-2}$, and 60 s and 1 repeats for 10-25 cd·s $m^{-2}$. There was a 60 see gap between each train of light flashes.

Photopic ERGs were recorded on week 4 and week 12 post-injection after light-adaptation at a background luminance of 30 cd·s $m^{-2}$. ERG recordings were obtained using a single-flash intensity series by the presentation of 1-ms flashes at the following intensities (all in cd·s $m^{-2}$): 0.3, 1, 3, 10, and 25. Each stimulus was repeated 32 times (for subsequent averaging), with a time interval between flashes of 0.5 s. There was a 60 see gap between each train of light flashes. The maximum amplitudes and implicit times for the a- and b-waves were extracted from the ERG responses as detailed in (Collison, F. T., J. C. Park, G. A. Fishman, E. M. Stone, and J. J. McAnany, Two-color pupillometry in KCNV2 retinopathy. *Doc Ophthalmol*, 2019, 139(1), p. 11-20. doi: 10.1007/s10633-019-09691-w), incorporated herein by reference in its entirety.

4. Optical Coherence Tomography (OCT)

OCT imaging was carried out at 0-3 days after the injection, at 2 weeks post injection and at 12 weeks post-injection in order to assess whether treatment improved overall thickness of retinal layers compared to untreated or sham treated eyes.

Mice were anesthetized and pupils dilated as described before. OCT was performed with a spectral domain optical coherence tomography system (Bioptigen Envisu R2200 SD-OCT system). Retinal layer thickness was measured using Bioptigen and ImageJ software.

5. Histopathology 5.1 Sectioning

Eyes were collected from treated mice and PBS injected mice at 12 weeks post-injection. Briefly, eyes were fixed in 4% PFA, for 1 h on ice. Cornea and lens were dissected and eyes were then incubated in 20% sucrose overnight at 4° C. The following day eyes were frozen in optimal cutting temperature compound and stored at −20° C. before sectioning. Retinal sections were collected on super-frost slides (Hurst) and cut using a Leica Cryostat CM3050 at 14 µm. Eyes were sectioned on the sagittal plane and sections collected sequentially across 10 slides. After sectioning slides were stored at −20° C. prior to further analysis.

5.2 Immunohistochemistry

The presence of Kv8.2 protein was assessed in situ using a Kv8.2 antibody (Antibodies Inc, USA, Cat 75-435/73-435) according to protocols published in (Skarnes, W. C., B. Rosen, A. P. West, M. Koutsourakis, W. Bushell, V. Iyer, A. O. Mujica, M. Thomas, J. Harrow, T. Cox, D. Jackson, J. Severin, P. Biggs, J. Fu, M. Nefedov, P. J. de Jong, A. F. Stewart, and A. Bradley, A conditional knockout resource for the genome-wide study of mouse gene function. *Nature*, 2011, 474(7351), p. 337-42. doi: 10.1038/nature 10163) in frozen retinal sections from the treated group, sham injected, uninjected KCNV2−/− and uninjected wildtype retinas of the corresponding age. We also evaluated in situ expression of rhodopsin (Rho) (Abcam, Cat #Ab3424) and cone arrestin (Arr3) (Millipore, Cat #AB15282).

6.0 Gene Expression Via Qualitative Real-Time Polymerase Chain Reaction (qRT-PCR)

Total RNA from retinas of treated mice and sham treated mice were extracted at 12 weeks post-injection using Trizol reagent and follow published protocols. RNA samples were then transcribed into complementary DNA (cDNA) by reverse transcriptase using either the ProtoScript® II First Strand cDNA Synthesis Kit (NEB, Cat #E6560S) or the QuantiTect Reverse Transcription Kit (Qiagen Cat #205311) following the manufacturer's recommended protocols. The cDNA was then used as the template for the qRT-PCR reaction.

KCNV2, cone arrestin and rhodopsin expression levels were evaluated using Taqman based assays (Thermo Fisher) and Real-Time PCR detection machine (Bio-Rad CFX Connect Real-Time System).

Statistical Analysis of Data

Retinal layers thickness form OCT imaging, maximum amplitudes and implicit times for the a- and b-waves from the ERG responses, retinal layers' thickness form histology, and mRNA expression levels of KCNV2, cone arrestin and rhodopsin from qRT-PCR from treated, PBS treated and untreated eyes were compared by obtaining mean and standard deviation values. Statistical significance was evaluated by the application standard t-test/one way ANOVA.

Example 2

Figure 5:
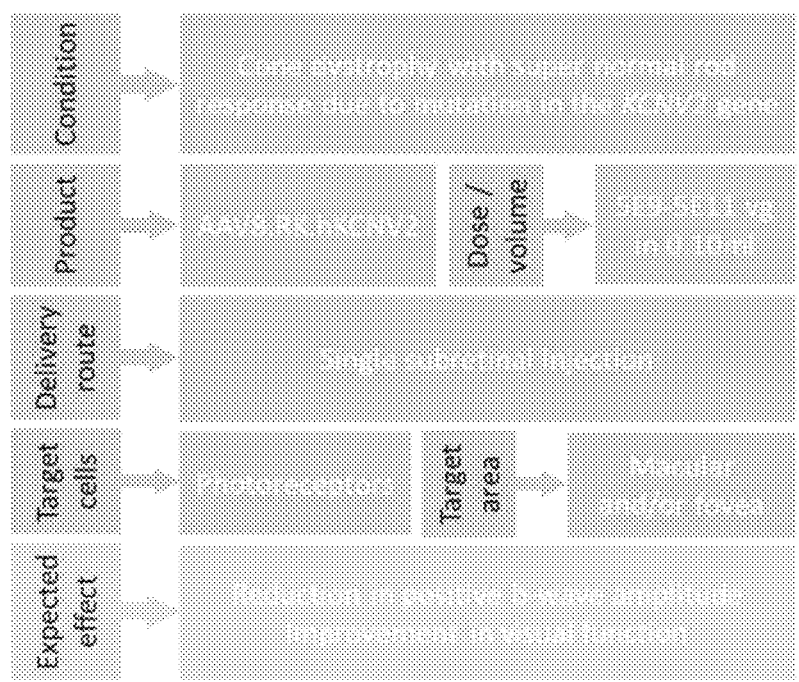
FIG. 5 shows an exemplary method of restoring retinal function.

Turning to FIG. 5, we illustrate an exemplary method for restoring retinal function. Cone dystrophy with super normal rod response, e.g., due to mutation in the KCNV2 gene is the target condition. In one example, the therapeutic intervention is the AAV8.RK.hKCNV2 (SEQ ID NO: 3), which in this case would be the codon optimized KCNV2 disclosed as SEQ ID NO: 2. An exemplary dosing regime is shown as 5E9-5E11vg in 0.10 ml delivered in one or more subretinal injections. As discussed herein, the design of the vector specifically targets gene expression to the photoreceptor cells and more specifically to expression in the macular and/or foveal area of the retina. The expected outcome is reduction in positive b-wave amplitude which is correlated with improvement in visual function.

Example 3

Figure 6:
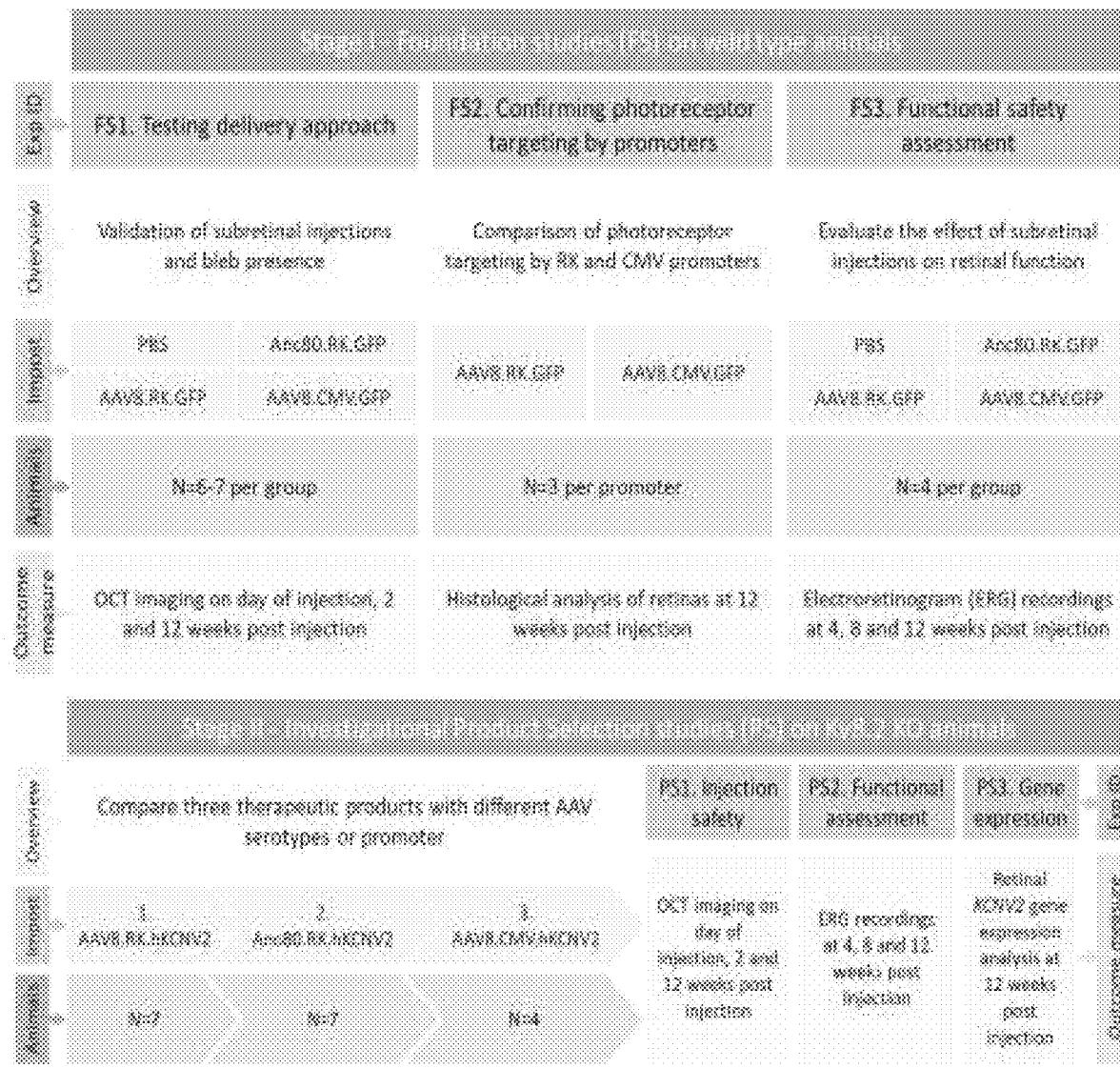
FIG. 6 provides the Stage I and Stage II investigational process.

Turning to FIG. 6, we provide an outline of the proof of concept studies. Stage 1 is foundation studies on wild-type animals. This comprises first testing the delivery approach and validating utility of the subretinal injections (designated at FS1). The injection of liquid into the subretinal space produces a bleb, a temporal and focal separation of the photoreceptors of its supporting retinal pigment epithelium (RPE). The timing of bleb resolution is an indicator of photoreceptor function. Outcomes are measured using OCT imaging on day of injection, as well as at 2-weeks and 12-weeks post injection. Optical coherence tomography (OCT) is a non-invasive imaging test. OCT imaging uses light waves to take cross-section pictures of the retina. This permits visualization of the retina's distinctive layers, to map the layers and to measure layer thickness.

After validation of the delivery approach, desired promoter targeting to photoreceptors is confirmed (designated FS2). The RK and CMV promoters are compared to determine the respective ability of each to target photoreceptors. Outcomes are measured in this case by histological analysis of retinas at twelve (12) weeks post injection.

Assessment of Functional Safety is performed to evaluate the effect of subretinal injections on retinal function (designated FS3). Outcomes are measured by electroretinogram (ERG) recordings at 4, 8 and 12 weeks post injection.

Stage II involves the Investigational Product Selection Studies on Kv8.2 KO animals. In this stage, three therapeutic products are compared, each with different AAV serotypes and promoters. The three therapeutic products are, e.g., AAV8.RK.hJCVN2, Anc80.RK.hKCNV2, and AAV8.CMV.hKCNV2. Outcomes with respect to injection safety are measured by OCT imaging on the day of injection, 2 and 12 weeks post injection. Outcomes with respect to functional assessment are measured by ERG recordings at 4, 8, and 12 weeks post injection. Outcomes with respect to gene expression are measured by retinal KCNV2 gene expression analysis at 12 weeks post injection.

Figure 7:
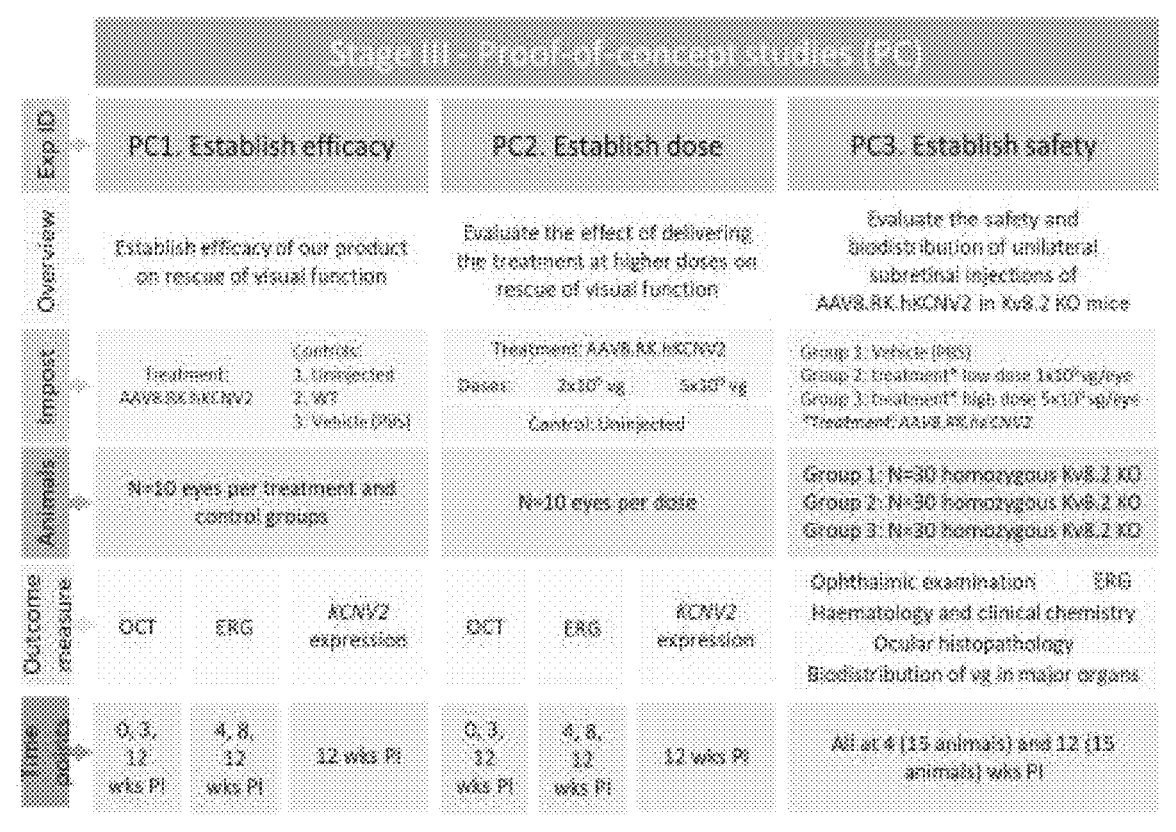

Turning to FIG. 7, we outline Stage III, proof of concept studies. At PC1 we establish efficacy of the vector expressing the optimized KCNV2 gene of SEQ ID NO: 2. Treatment protocol as outlined in Example 1 above. Controls include uninjected mice, wild type mice which are injected subretinally with the product. These are compared with Kv8.2 KO animals that are injected with the treatment, AAV8.RK.hKCNV2 (e.g., SEQ ID NO: 3). Outcomes are measured by OCT (at 0, 3, and 12 weeks post injection), ERG (at 4, 8, and 12 weeks post injection) and KCNV2 gene expression data (at 12 weeks post injection). At PC2, restoration of visual function is evaluated to look at the effect of delivering the treatment at higher doses. Here, the treatment AAV8.RK.hKCNV2 (e.g., SEQ ID NO: 3) is injected subretinally with two dosage regimes: 2×10 9 vg and 5×10 9 vg. The control is uninjected mice. Outc Outcomes are measured by OCT (at 0, 3, and 12 weeks post injection), ERG (at 4, 8, and 12 weeks post injection) and KCNV2 gene expression data (at 12 weeks post injection). At PC3, safety and biodistribution are evaluated. We evaluate the safety and biodistribution of unilateral subretinal injections of AAV8.RK.hKCNV2 (e.g., SEQ ID NO: 3) in Kv8.2 KO animals. There are three treatment groups which receive the treatment by subretinal injection: Group 1 which receives only the vehicle which is PBS; Group 2, which receives the treatment at a dose of 1×10^9 vg/eye; and Group 3, which receives the treatment at a dose of 5×10^9 vg/eye. All animals are homozygous Kv8.2 KO. Outcomes are measured by ophthalmic examination, ERG, haematology and clinical chemistry, ocular histopathology, and biodistribution of vg in major organs. The animals are examined at 4 and 12 weeks post injection.

Overall, the data from these foundational studies were used to guide the decision of which three potential therapeutic products would be used. Based on the gene expression data, the disclosed SEQ ID NO: 2 showed an average of an 8-fold gene expression increase compared to wild type KCNV2. The ERG positive b-wave data showed a higher difference and significant decrease compared to untreated eyes compared to the other products tested. Therefore, AAV8.RK.hKCNV2 vector (SEQ ID NO: 3) was chosen as the therapeutic treatment product.

Selected Results

Functional ERG Analysis of Treated Eyes Compared to Wild Type

Figure 8:
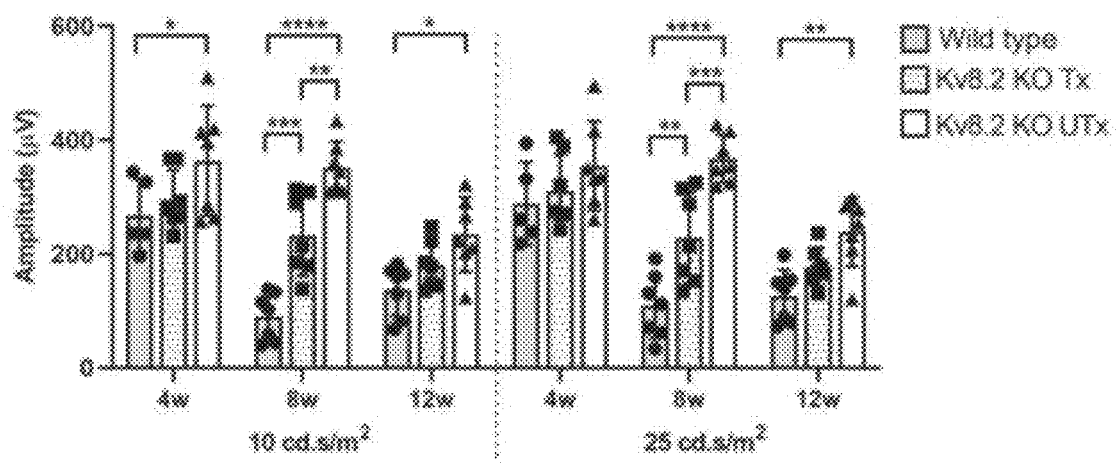
FIG. 8 provides a comparison between treated and untreated mice using the disclosed method, system, and nucleic acid sequence.

Turning to FIG. 8, as discussed FIG. 8 provides a comparison between treated and untreated mice using the disclosed method, system, and nucleic acid sequence. To evaluate efficacy of treatment with SEQ ID NO: 2 and further with vector SEQ ID NO: 3 to restore photoreceptor function in a subject (such as a subject with CDSRR), positive b-wave ERG amplitude was compared between treated (CDSRR animal represented by Kv8.2 animal), untreated (CDSRR animal represented by Kv8.2 animal), and wild type eyes (wildtype animal). Average positive b-wave amplitude comparison between Kv8.2 KO mice treated with AAV8.Rk.hKCNV2 (Kv8.2 KO Tx), untreated Kv8.2 KO mice (Kv8.2 KO UTx) and wild type untreated at 4, 8 and 12 weeks post injection. Data is shown at two different stimulus intensities (10 and 25 cd·s/m$^2$). Data shown as mean±SD and statistical significance done by two-way ANOVA with Turkey's correction. *P<0.024; P<0.003, *P<0.0003 and P<0.0001. As shown in this FIG. 8, one subretinal injection of SEQ ID NO: 2, and further, SEQ ID NO: 3, was sufficient to significantly decrease the supernormal positive b-wave compared to the untreated eye. The b-wave measures the time between the flash and the peak of the response or electrical activity of the retina in response to a light stimulus. This data supports restoration of photoreceptor function by SEQ ID NO: 2 and further SEQ ID NO: 3, as the retina response time decreases over time in treated Kv8.2 KO animals as compared to Kc8.2 untreated animals.

Retinal Gene Expression Following Treatment

Figure 9:
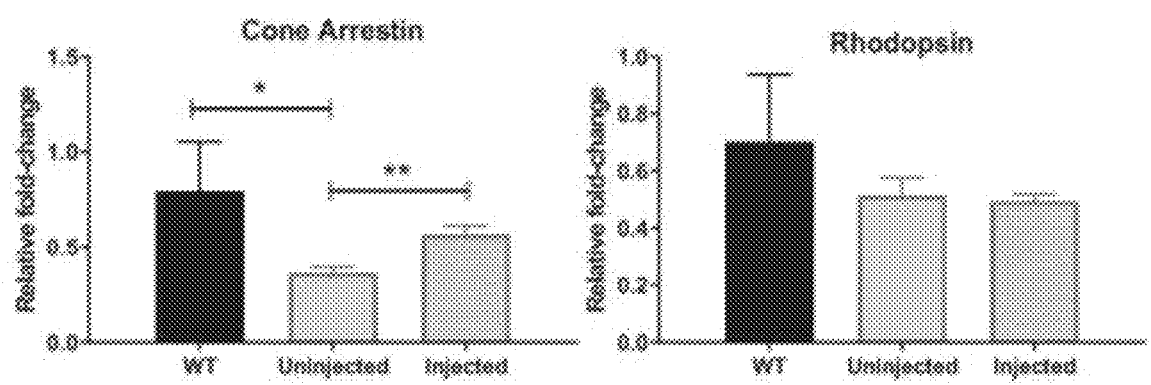
FIG. 9 illustrates relative gene expression of a cone (A, cone arrestine) and rod (B, rhodopsin) markes in wild type (WT), uninjected versus treated retinas *P<0.05; *P<0.01.

FIG. 9 illustrates relative gene expression of a cone (a, cone arrestine) and rod (B, rhodopsin) markes in wild type (WT), uninjected versus treated retinas *P<0.05; *P<0.01. To further evaluate efficacy of treatment with SEQ ID NO: 2 and further with vector SEQ ID NO: 3 to restore photoreceptor function in a subject (such as a subject with CDSRR), on rod and cone health, the levels of gene expression for rhodopsin and cone arrestin were evaluated. Rhodopsin is a marker for rod health. Arrestin is a marker for cone health. FIG. 9 shows expression levels of rhodopsin and cone arrestin in Wild Type, uninjected Kv8.2 animals and injected Kv8.2 animals. This data demonstrates that treatment with SEQ ID NO: 2 and further with SEQ ID NO: 3 resulted in gene expression of cone arrestin. Cone arrestin showed a statistically significant increase in gene expression levels after treatment compared to untreated retinas. Although rhodopsin levels looked decreased compared to WT in both treated and untreated retinas, this was not statistically significant.

Figure 10:
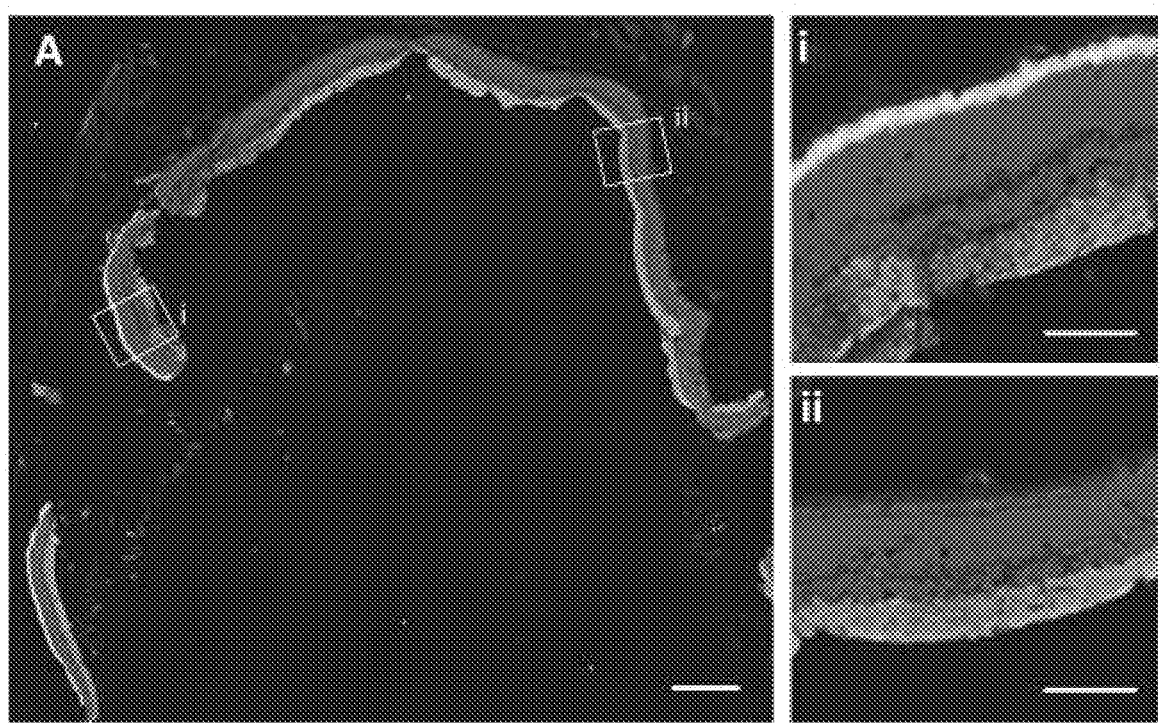
FIG. 10 shows representative images of retinal expression of human Kv8.2 subunit in retinas of Kv8.2 KO mice injected with SEQ ID NO: 2 as delivered by SEQ ID NO: 3, at 12 weeks post-treatment.

Turning to FIG. 10, histological analysis and immunohistochemistry labeling of Kv8.2 subunits using an antibody against human KCNV2 peptide showed expression within the injected part of the retina while the untreated area showed no expression of Kv8.2 protein. Specifically, FIG. 10 shows representative images of retinal expression of human Kv8.2 subunit in retinas of Kv8.2 KO mice injected with SEQ ID NO: 2 as delivered by SEQ ID NO: 3, at 12 weeks post-treatment. (A) Wide-field view of retinal sections showing treated area to the left and untreated to the right. Scale bar=200 µM. (i) Higher magnification inset of treated area showing expression of human Kv8.2. (ii) Inset of untreated area showing no Kv8.2 expression. Scale bar for (i) and (ii)=25 µM.

Functional ERG Analysis of Treated Eyes Compared to Wild Type

Figure 12:
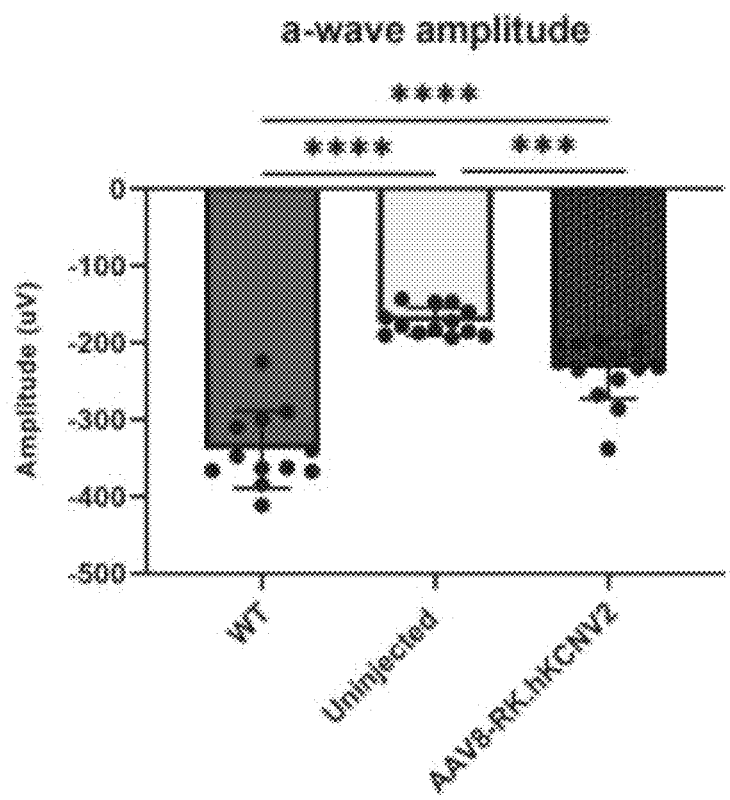
FIG. 12 shows data representing the a-wave amplitude of treated versus untreated mice.
Figure 13:
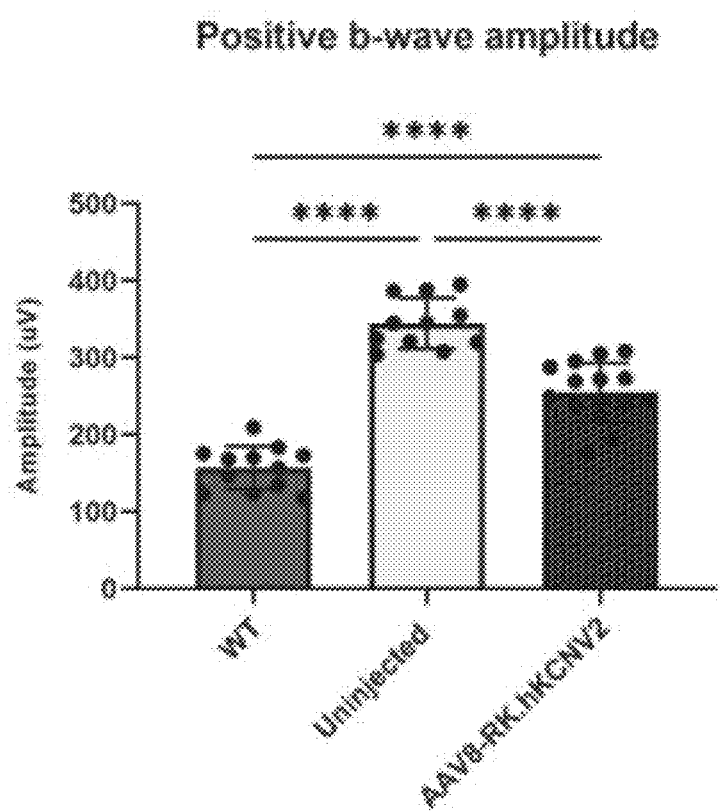
FIG. 13 shows data representing the positive b-wave amplitude of treated versus untreated mice.

FIG. 12 and FIG. 13 provides a comparison between treated and untreated mice using the disclosed method, system, and nucleic acid sequence. To evaluate efficacy of treatment with SEQ ID NO: 2 and as delivered in the vector of SEQ ID NO: 3 to restore photoreceptor function in a subject (such as a subject with CDSRR), the a-wave amplitude and positive b-wave ERG amplitude was compared between treated (CDSRR animal represented by Kv8.2 animal), untreated (CDSRR animal represented by Kv8.2 animal), and wild type eyes (wildtype animal). Quantification of scotopic (rod-meditated) electroretinogram (ERG) recordings of wildtype (WT), Kv8.2 KO untreated (uninjected) and Kv8.2 KO eyes treated subretinally with 5e9 viral genomes of therapeutic product AAV8.RK.hKCNV2 (SEQ ID NO: 3). Recordings were obtained at 4 weeks post-treatment or equivalent age-matched controls. WT, n=12; Uninjected, n=11; AAV8.RK.hKCNV2, n=12. Two-way ANOVA with Tukey's multiple comparisons test, $*p<0.05$, $p<0.005$, $*p<0.0005$, $****p<0.0001$. The data demonstrates that the treatment with SEQ ID NO: 2 as delivered in the vector of SEQ ID NO: 3 restores photoreceptor function in a subject, such as a subject with CDSRR as represented by a Kv8.2 KO animal).

Figure 14:
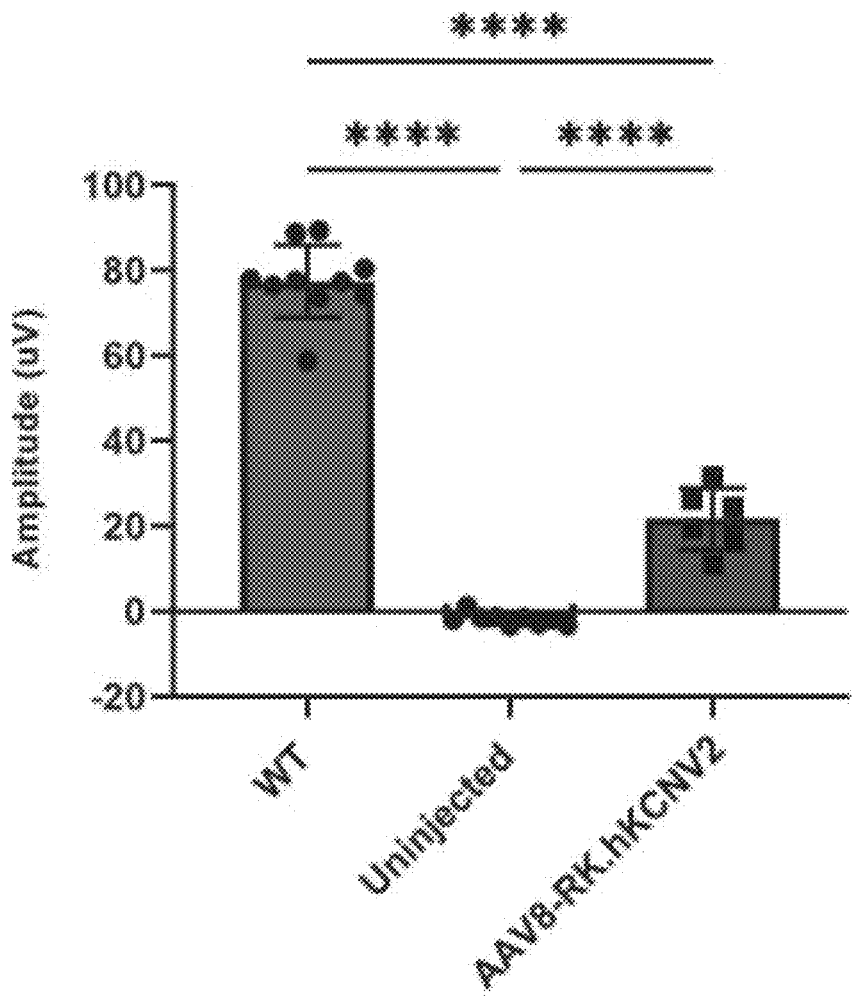
FIG. 14 shows OCT data of treated and untreated mice.

FIG. 14 demonstrates Quantification of scotopic oscillatory potential 1 (OP1) at 25 cd·s/m2 from wildtype (WT), Kv8.2 KO untreated (uninjected) and Kv8.2 KO eye treated subretinally with 3e9 viral genomes of therapeutic product AAV8.RK.hKCNV2. Recordings were obtained at 12 weeks post-treatment or equivalent age-matched controls. WT, n=10; Uninjected, n=6; AAV8.RK.hKCNV2, n=6. Two-way ANOVA with Tukey's multiple comparisons test, $****p<0.0001$. The data demonstrates that the treatment with SEQ ID NO: 2 as delivered in the vector of SEQ ID NO: 3 restores photoreceptor function in a subject, such as a subject with CDSRR as represented by a Kv8.2 KO animal).

Figure 15:
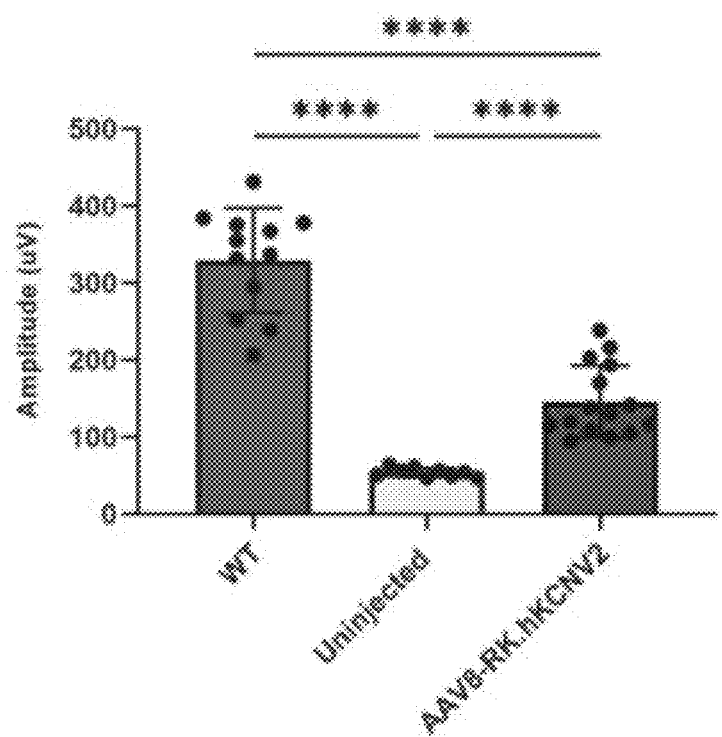
FIG. 15 demonstrates quantification of c-wave from wild-type (WT), Kv8.2 KO untreated (uninjected) and Kv8.2 KO eye.

FIG. 15 demonstrates quantification of c-wave from wildtype (WT), Kv8.2 KO untreated (uninjected) and Kv8.2 KO eye treated subretinally with 5e9 viral genomes of therapeutic product AAV8.RK.hKCNV2. Recordings were obtained at 4 weeks post-treatment or equivalent age-matched controls. WT, n=12; Uninjected, n=9; AAV8.RK.hKCNV2, n=15. Two-way ANOVA with Tukey's multiple comparisons test, $****p<0.0001$. The data demonstrates that the treatment with SEQ ID NO: 2 as delivered in the vector of SEQ ID NO: 3 restores photoreceptor function in a subject, such as a subject with CDSRR as represented by a Kv8.2 KO animal).

Optomotor Behavioural Response

Figure 16:
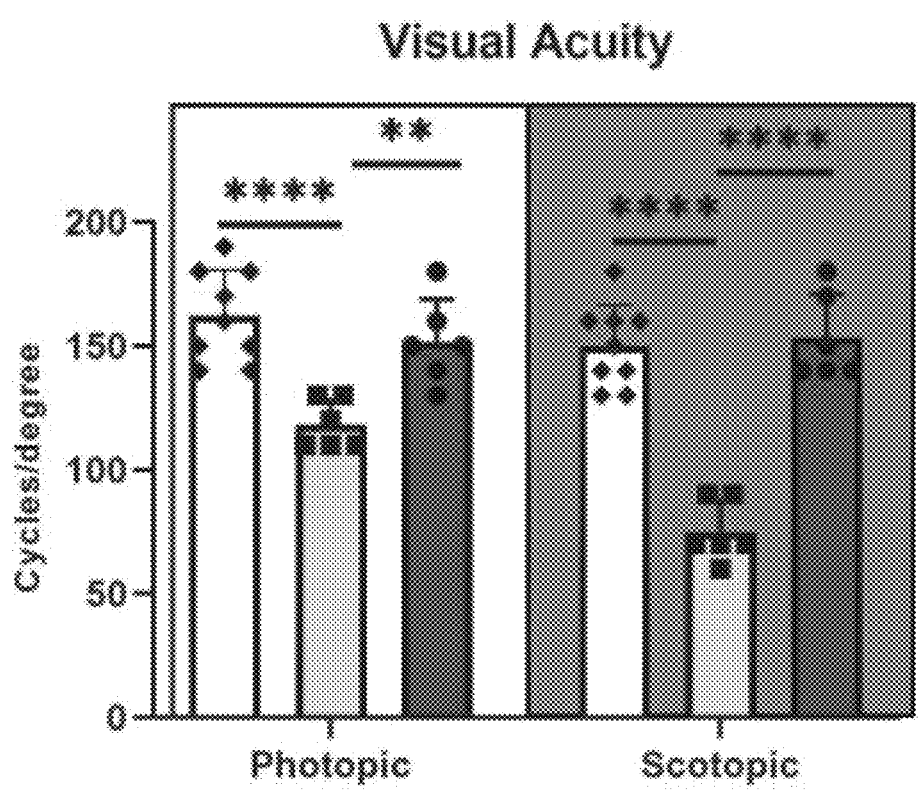
FIG. 16 demonstrates improved photopic and scotopic visual acuity and scotopic contrast sensitivity of treated Kv8.2 KO mice at 12 weeks post-treatment.

FIG. 16 demonstrates improved photopic and scotopic visual acuity and scotopic contrast sensitivity of treated Kv8.2 KO mice at 12 weeks post-treatment. Treated animals were given a 3e9 viral genome dose subretinally of AAV8.RK.hKCNV2 (n=3-6) and compared to age-matched untreated (uninjected, n=3-5) and WT (n=8) animals. Two-way ANOVA, Sidak's multiple comparison post-hoc, $p=0.0015$, $**p<0.0001$. WT vs treated AAV8.RK.hKCNV2 was non-significant.

Gene and Protein Expression Data

Figure 17:
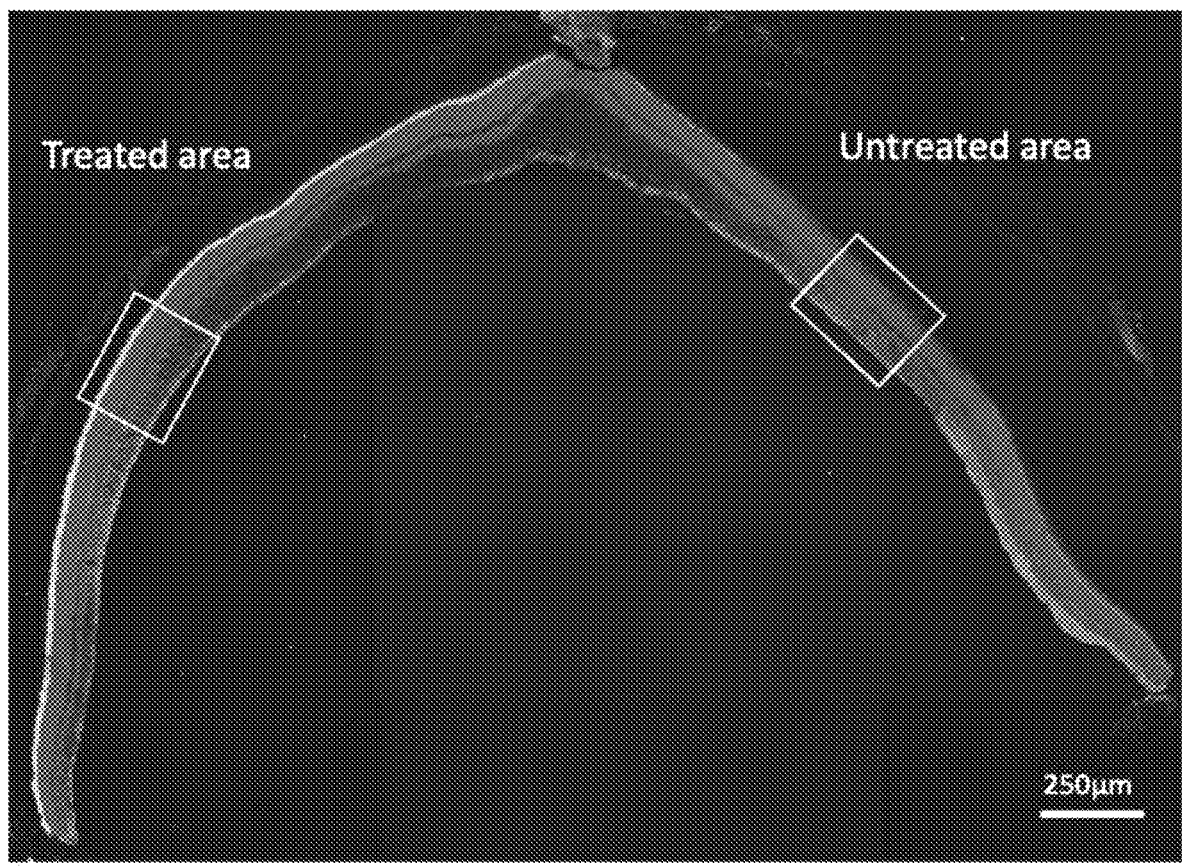
FIG. 17 is an overview of retinal section from a subretinally injected eye with treated area showing expression of human Kv8.2 subunit (green) and untreated area with no Kv8.2 expression.
Figure 18:
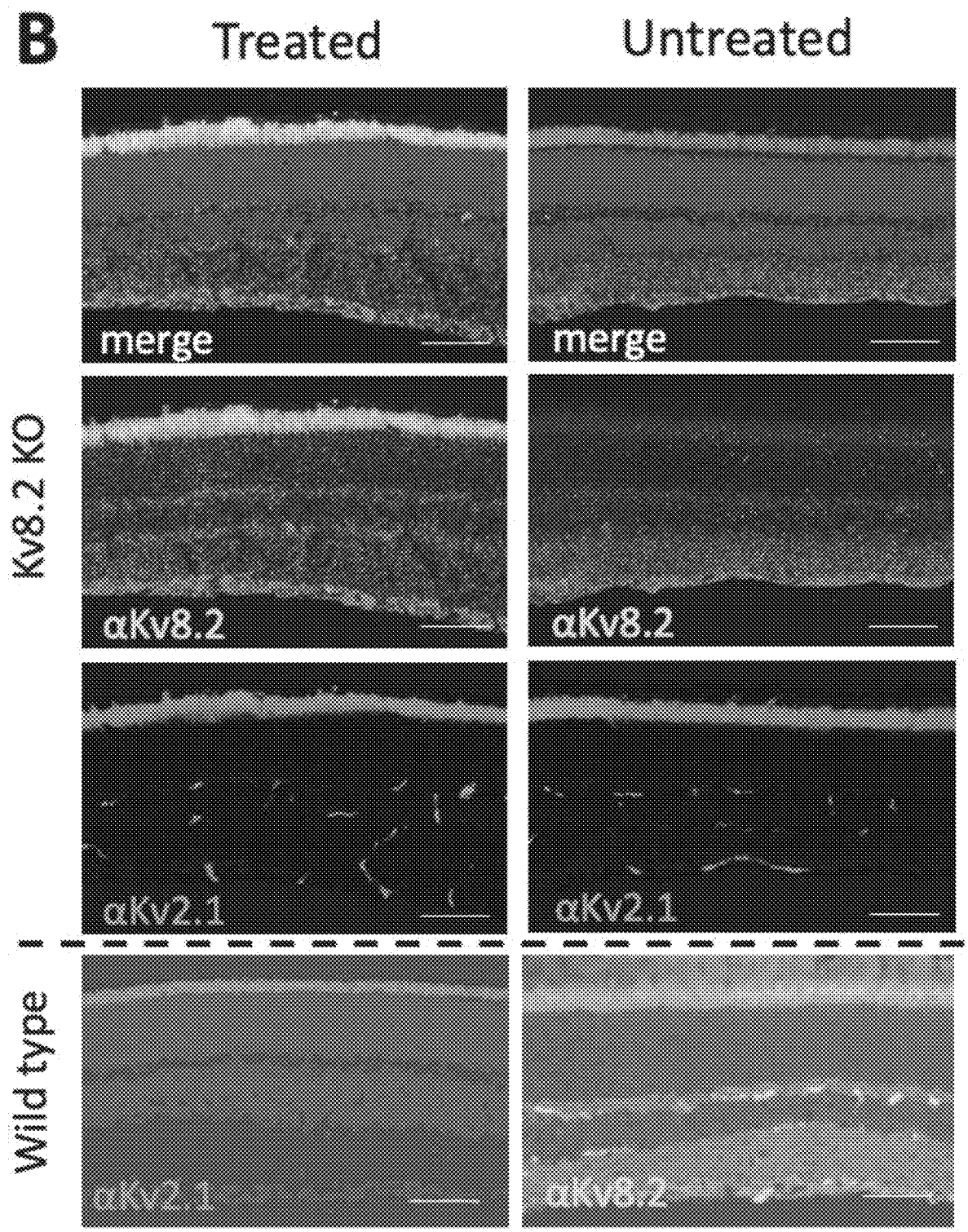
FIG. 18 provides higher magnification images of treated and untreated areas showing Kv8.2 expression (green), Kv2.1 expression (red) and cell nuclei (blue). Scale bar=50 µm.'
Figure 19:
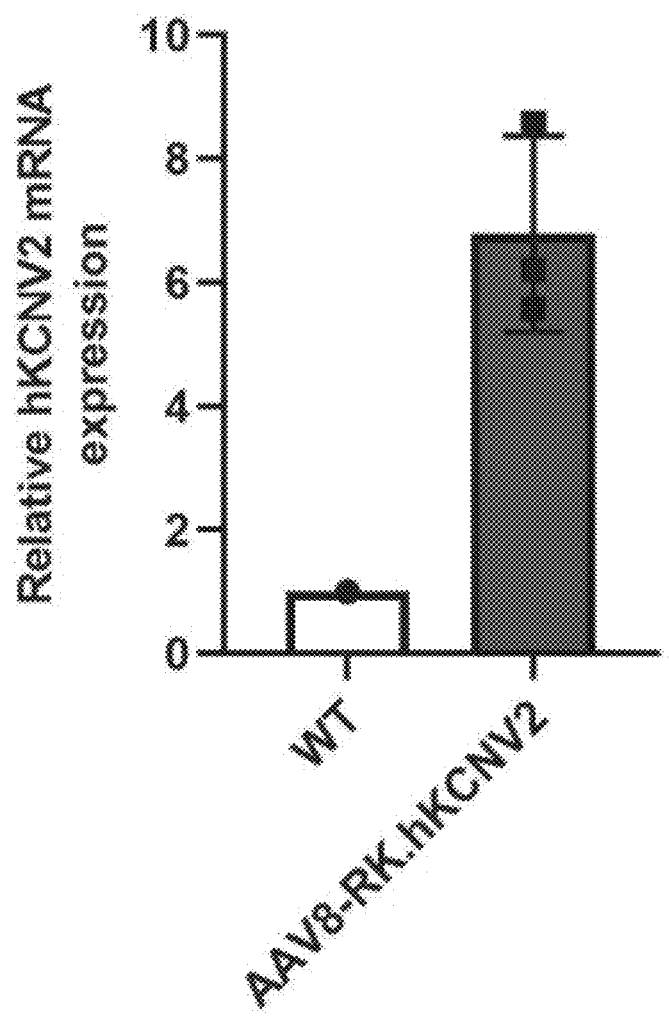
FIG. 19 provides data from real-time quantitative PCR showing expression of human KCNV2 gene in treated eyes normalised to wild type.

FIG. 17, FIG. 18, and FIG. 19 are histological data showing Kv8.2 protein and KCNV2 gene expression in treated Kv8.2 KO eye at 12 weeks post-treatment. FIG. 17 is an overview of retinal section from a subretinally injected eye with treated area showing expression of human Kv8.2 subunit (green) and untreated area with no Kv8.2 expression. FIG. 18 provides higher magnification images of treated and untreated areas showing Kv8.2 expression (green), Kv2.1 expression (red) and cell nuclei (blue). Scale bar=50 µm. FIG. 19 provides data from real-time quantitative PCR showing expression of human KCNV2 gene in treated eyes normalised to wild type. N=3 eyes.

FIG. 20 and FIG. 21 provide a sequence alignment demonstrating the comparison of the human KCNV2 coding region (SEQ ID NO: 12) and the optimized KCNV2 (SEQ ID NO: 2) disclosed herein. The top row contains the nucleic acids of human KCNV2 (SEQ ID NO: 12). The bottom row contains the nucleic acids of SEQ ID NO: 2. SEQ ID NO: 2 shares approximately 76% identity with human SEQ ID NO: 12.

It will be apparent that the precise details of the methods or compositions described may be varied or modified without departing from the spirit of the described embodiments. We claim all such modifications and variations that fall within the scope and spirit of the claims below.

We claim:

1. A modified KCNV2 nucleotide sequence as set forth in SEQ ID NO: 2, said sequence coding the peptide of SEQ ID NO: 11, said sequence capable of restoring photoreceptor activity.

2. A vector comprising the modified KCNV2 nucleotide sequence of claim 1.

3. The vector of claim 2, wherein the vector is a viral vector.

4. The vector of claim 3, wherein the viral vector is an AAV vector.

5. The vector of claim 2, wherein the vector is a gamma-retroviral vector, a lentiviral vector, or an adenoviral vector.

6. The vector of claim 4 having the nucleotide sequence of SEQ ID NO: 3.

7. The vector of claim 6, further comprising at least one of an RK promoter, KOZAK consensus sequence, a Woodchuck Hepatitis Virus (WHP) Posttranscriptional Regulatory Element (WPRE), and a bovine growth hormone polyadenylation (BGH poly(A)) signal.

8. The vector of claim 7, wherein the RK promoter, the KOZAK consensus sequence, SEQ ID NO: 2, the WPRE, and the BGH poly(A) signal are arranged in 5' to 3' order.

9. A nucleotide sequence comprising a KCNV2 nucleotide sequence as set forth in SEQ ID NO: 2 operably linked to an RK promoter, said nucleotide sequence encoding a protein of SEQ ID NO: 11, said protein of SEQ ID NO: 11 having a photoreceptor activity.

10. The KCNV2 nucleotide sequence of claim 9, wherein said nucleotide sequence is operably linked to a KOZAK sequence, a WPRE, and a BGH poly(A) signal.

11. A pharmaceutical composition, comprising the vector of claim 2, in a pharmaceutically acceptable vehicle.

12. The pharmaceutical composition of claim 11 that is formulated for local, systemic, or topical administration.

13. The pharmaceutical composition of claim 11 that is formulated for oral, nasal, pulmonary, buccal, transdermal, subcutaneous, intraduodenal, enteral, parenteral, intravenous, or intramuscular administration.

* * * * *